(12) United States Patent
Collins et al.

(10) Patent No.: US 9,840,720 B2
(45) Date of Patent: Dec. 12, 2017

(54) MATERIALS AND METHODS RELATING TO PACKAGING CELL LINES

(71) Applicant: UCL Business PLC, London (GB)

(72) Inventors: Mary Collins, London (GB); Yasuhiro Takeuchi, London (GB); Sean Knight, Addlestone (GB)

(73) Assignee: UCL Business PLC, London (GB)

( * ) Notice: Subject to any disclaimer, the term of this patent is extended or adjusted under 35 U.S.C. 154(b) by 0 days.

(21) Appl. No.: 14/378,532

(22) PCT Filed: Feb. 13, 2013

(86) PCT No.: PCT/GB2013/050335
§ 371 (c)(1),
(2) Date: Nov. 21, 2014

(87) PCT Pub. No.: WO2013/121194
PCT Pub. Date: Aug. 22, 2013

(65) Prior Publication Data
US 2015/0023933 A1 Jan. 22, 2015

(30) Foreign Application Priority Data
Feb. 13, 2012 (GB) .................................. 1202516.9

(51) Int. Cl.
| | | |
|---|---|---|
| *C12N 5/10* | (2006.01) | |
| *C12N 15/48* | (2006.01) | |
| *C12N 15/63* | (2006.01) | |
| *C12N 15/867* | (2006.01) | |
| *C12N 15/86* | (2006.01) | |
| *C12N 7/00* | (2006.01) | |
| *A61K 48/00* | (2006.01) | |

(52) U.S. Cl.
CPC ............ *C12N 15/86* (2013.01); *A61K 48/005* (2013.01); *C12N 7/00* (2013.01); *A61K 48/00* (2013.01); *C12N 2740/16043* (2013.01); *C12N 2740/16044* (2013.01); *C12N 2740/16052* (2013.01); *C12N 2740/16222* (2013.01)

(58) Field of Classification Search
USPC ...................................... 435/455, 325, 320.1
See application file for complete search history.

(56) References Cited

U.S. PATENT DOCUMENTS

| | | |
|---|---|---|
| 5,793,909 A | 8/1998 | Leone et al. |
| 6,136,597 A | 10/2000 | Hope et al. |
| 6,168,953 B1 | 1/2001 | Dropulic et al. |
| 6,207,426 B1 | 3/2001 | Dropulic et al. |
| 6,218,181 B1 | 4/2001 | Verma et al. |
| 6,232,120 B1 | 5/2001 | Dropulic et al. |
| 6,235,522 B1 | 5/2001 | Kingsman et al. |
| 6,284,469 B1 | 9/2001 | Hope et al. |
| 6,312,682 B1 | 11/2001 | Kingsman et al. |
| 6,312,683 B1 | 11/2001 | Kingsman et al. |
| 6,498,033 B1 | 12/2002 | Dropulic et al. |
| 6,669,936 B2 | 12/2003 | Kingsman et al. |
| 6,924,123 B2 | 8/2005 | Kingsman et al. |
| 6,924,144 B2 | 8/2005 | Naldini et al. |
| 7,198,784 B2 | 4/2007 | Kingsman et al. |
| 7,351,585 B2* | 4/2008 | Mitrophanous ........ C12N 15/86 435/320.1 |
| 7,419,829 B2 | 9/2008 | Mitrophanous et al. |
| 7,700,342 B2 | 4/2010 | Kaleko et al. |
| 8,709,977 B2 | 4/2014 | Jenkins |
| 2006/0084093 A1 | 4/2006 | Lee et al. |
| 2006/0258006 A1* | 11/2006 | Mitrophanous ........ C12N 15/86 435/456 |
| 2008/0089863 A1 | 4/2008 | Mallet et al. |
| 2011/0200568 A1* | 8/2011 | Ikeda ................... C12N 5/0696 424/93.21 |
| 2012/0164118 A1 | 6/2012 | Trobridge et al. |

FOREIGN PATENT DOCUMENTS

| | | |
|---|---|---|
| EP | 0 846 182 B1 | 6/1998 |
| EP | 1 373 536 B9 | 5/2008 |
| WO | 94/29440 | 12/1994 |
| WO | 00/15819 | 9/1999 |
| WO | 00/52188 | 9/2000 |
| WO | 02/072851 A3 | 9/2002 |
| WO | 2004/110485 A1 | 12/2004 |
| WO | 2007/091066 A1 | 8/2007 |
| WO | 2009/019612 A2 | 2/2009 |
| WO | 2009/127537 A1 | 10/2009 |
| WO | 2009/131706 A1 | 10/2009 |
| WO | 2010/054141 A2 | 5/2010 |
| WO | 2010/129602 A2 | 11/2010 |

OTHER PUBLICATIONS

Ikeda et al Continuous high-titer HIV-1 vector production Nature Biotechnology 21, 569-572 (2003).*
Karreman et al., On the use of double FLP recognition targets (FRTs) in the LTR of retroviruses for the construction of high producer cell lines 1616-1624 Nucleic Acids Research, 1996, vol. 24, No. 9.*
Vanin et al Journal of Virology Development of High-Titer Retroviral Producer Cell Lines by Using Cre-Mediated Recombination Oct. 1997, p. 7820-7826.*
Sanber et al Construction of stable packaging cell lines for clinical lentiviral vector production pp. 1-9 Scientific Reports | 5 : 9021.*
Arai et al., A new system for stringent, high-titer vesicular stomatitis virus G protein-pseudotyped retrovirus vector induction by introduction of Cre recombinase into stable prepackaging cell lines J Virol. Feb. 1998;72(2):1115-21.*

(Continued)

*Primary Examiner* — Maria Leavitt
(74) *Attorney, Agent, or Firm* — Kathleen D. Rigaut; Dann, Dorfman, Herrell and Skillman, P.C.

(57) ABSTRACT

Lentiviral packaging cells and methods for producing the same are provided herein. Specifically, lentiviral packaging cells capable of producing lentiviral vector suitable for use in clinical trials are provided. Methods for producing lentiviral packaging cells capable of producing lentiviral vector suitable for use in clinical trials are described.

14 Claims, 23 Drawing Sheets

(56) References Cited

OTHER PUBLICATIONS

NCBI "HIV capsid protein" pp. 1-2 downloaded May 11, 2016.*
Retroviral Psi packaging element From Wikipedia, the free encyclopedia downloaded Feb. 15, 2017.*
Verhoeyen et al., Evaluation of Retroviral Vector Design in Defined Chromosomal Loci by Flp-Mediated Cassette Replacement Human Gene Therapy 12:933-944 (May 20, 2001).*
Sanber et al 2015 Construction of stable packaging cell lines for clinical lentiviral vector production Scientific Reports pp. 1-101.*
Strang et al Characterization of HIV-1 vectors with gammaretrovirus envelope glycoproteins produced from stable packaging cells Gene Therapy (2004) 11, 591-598.*
Arai, Tohru et al., "A New System for Stringent, High-Titer Vesicular Stomatitis Virus G Protein-Pseudotyped Retrovirus Vector Induction by Introduction of Cre Recombinase into Stable Prepackaging Cell Lines", Journal of Virology, 72(2): 1115-1121 (1998).
Carrondo, Manuel et al., "Integrated Strategy for the Production of Therapeutic Retroviral Vectors", Human Gene Therapy, 22: 370-379 (2011).
Farson, Deborah et al., "A New-Generation Stable Inducible Packaging Cell Line for Lentiviral Vectors", Human Gene Therapy, 12: 981-997 (2001).
Gama-Norton, Leonor et al., "Lentivirus Production is Influenced by SV40 Large T-Antigen and Chromosomal Integration of the Vector in HEK293 Cells", Human Gene Therapy, 22: 1269-1279 (2011).
Ikeda, Yasuhiro et al., "Continuous high-titer HIV-1 vector production", Nature Biotechnology, 21: 569-572 (2003).
Murphy, Stephen J. et al., "Novel Integrating Adenoviral/Retroviral Hybrid Vector for Gene Therapy", Human Gene Therapy, 13: 745-760 (2002).
Ni, Yajin et al., "Generation of a packaging cell line for prolonged large-scale production of high-titer HIV-1-based lentiviral vector", The Journal of Gene Medicine, 7: 818-834 (2005).
Relander, Thomas et al., "Gene Transfer to Repopulating Human CD34+ Cells Using Amphotropic-, GALV-, or RD114-Pseudotyped HIV-1-Based Vectors from Stable Producer Cells", Molecular Therapy, 11(3): 452-459 (2005).
Strang, Blair L. et al., "Human Immunodeficiency Virus Type I Vectors with Alphavirus Envelope Glycoproteins Produced from Stable Packaging Cells", 79(3): 1765-1771 (2005).
Trobridge, Grant D. et al., "Cocal-pseudotyped Lentiviral Vectors Resist Inactivation by Human Serum and Efficiently Transduce Primate Hematopoietic Repopulating Cells", Molecular Therapy, 18(4): 725-733 (2010).

* cited by examiner

Optimised WinPac-RDpro-HV Titres With/Without Spinoculation

Figure 16

Titre Stability During Prolonged Culture

WinPac-RDpro-HV1 Titres Over Time

Figure 17

DNA Copy No. of Packaging Components and Vector Genome in WinPac Cells

RNA Expression Levels of Vector Components and Genome

```
                        SEQUENCE LISTING

<160> NUMBER OF SEQ ID NOS: 11

<210> SEQ ID NO 1
<211> LENGTH: 34
<212> TYPE: DNA
<213> ORGANISM: Artificial sequence
<220> FEATURE:
<223> OTHER INFORMATION: Synthetic sequence: loxP site

<400> SEQUENCE: 1
ataacttcgt ataatgtatg ctatacgaag ttat                               34

<210> SEQ ID NO 2
<211> LENGTH: 34
<212> TYPE: DNA
<213> ORGANISM: Artificial sequence
<220> FEATURE:
<223> OTHER INFORMATION: Synthetic sequence: loxP site with mutation in
      the left inverted repeat

<400> SEQUENCE: 2
taccgttcgt ataatgtatg ctatacgaag ttat                               34

<210> SEQ ID NO 3
<211> LENGTH: 34
<212> TYPE: DNA
<213> ORGANISM: Artificial sequence
<220> FEATURE:
<223> OTHER INFORMATION: Synthetic sequence: loxP site with mutation in
      the right inverted repeat

<400> SEQUENCE: 3
ataacttcgt ataatgtatg ctatacgaac ggta                               34

<210> SEQ ID NO 4
<211> LENGTH: 20
<212> TYPE: DNA
<213> ORGANISM: Artificial sequence
```

```
<220> FEATURE:
<223> OTHER INFORMATION: Synthetic sequence: Primer

<400> SEQUENCE: 4
tggacttcga gcaagagatg                                              20

<210> SEQ ID NO 5
<211> LENGTH: 20
<212> TYPE: DNA
<213> ORGANISM: Artificial sequence
<220> FEATURE:
<223> OTHER INFORMATION: Synthetic sequence: Primer

<400> SEQUENCE: 5
gaaggaaggc tggaagagtg                                              20

<210> SEQ ID NO 6
<211> LENGTH: 20
<212> TYPE: DNA
<213> ORGANISM: Artificial sequence
<220> FEATURE:
<223> OTHER INFORMATION: Synthetic sequence: Primer

<400> SEQUENCE: 6
aagagagctt caggtttggg                                              20

<210> SEQ ID NO 7
<211> LENGTH: 20
<212> TYPE: DNA
<213> ORGANISM: Artificial sequence
<220> FEATURE:
<223> OTHER INFORMATION: Synthetic sequence: Primer

<400> SEQUENCE: 7
tgccaaagag tgatctgagg                                              20

<210> SEQ ID NO 8
<211> LENGTH: 20
<212> TYPE: DNA
<213> ORGANISM: Artificial sequence
<220> FEATURE:
<223> OTHER INFORMATION: Synthetic sequence: Primer

<400> SEQUENCE: 8
tgtgcctctt cagctaccac                                              20

<210> SEQ ID NO 9
<211> LENGTH: 20
<212> TYPE: DNA
<213> ORGANISM: Artificial sequence
<220> FEATURE:
<223> OTHER INFORMATION: Synthetic sequence: Primer

<400> SEQUENCE: 9
caatatttga gggcttccca                                              20

<210> SEQ ID NO 10
<211> LENGTH: 20
<212> TYPE: DNA
<213> ORGANISM: Artificial sequence
<220> FEATURE:
<223> OTHER INFORMATION: Synthetic sequence: Primer

<400> SEQUENCE: 10
aactcccaac aggaatggtc                                              20
```

```
<210> SEQ ID NO 11
<211> LENGTH: 20
<212> TYPE: DNA
<213> ORGANISM: Artificial sequence
<220> FEATURE:
<223> OTHER INFORMATION: Synthetic sequence: Primer

<400> SEQUENCE: 11
ttaagtaggc cgtcttgcct                                              20
```

MATERIALS AND METHODS RELATING TO PACKAGING CELL LINES

The present application is §371 application of PCT/GB2013/050335 filed Feb. 13, 2013 which claims priority to GB Patent Application No. 1202516.9 filed Feb. 13, 2012, the entire disclosure of each being incorporated by reference herein.

FIELD OF THE INVENTION

The present invention concerns materials and methods for producing packaging cell lines. Particularly, but not exclusively, the invention is concerned with the development of a stable packaging cell line for lentiviral vectors.

BACKGROUND OF THE INVENTION

Lentiviruses or lentiviral vectors derived from them are popular as gene delivery vehicles.

The lentiviral genome includes three genes found in retroviruses, namely gag, pol and env, which are flanked by two long terminal repeat (LTR) sequences. The gag gene encodes internal structural proteins such as matrix, capsid and nucleocapsid proteins. The pol gene encodes the RNA-directed DNA polymerase (reverse transcriptase (RT)), a protease and an integrase, and the env gene encodes the viral envelope proteins. The 5' and 3' LTRs serve to promote transcription and polyadenylation of the viron RNAs. Adjacent to the 5'LTR are sequences necessary for reverse transcription of the genome such as the tRNA binding site and for efficient encapsidation of viral RNA into particles such as the Psi site.

Lentiviral vectors require an envelope protein in order to transduce a target cell. The envelope protein is expressed in the cell producing the vector and becomes incorporated into the vector particle. These particles comprise a protein core expressed by the gag gene which encases the viral RNA. This in turn is encased by a portion of the cell membrane that contains the envelope protein.

A lentiviral vector packaging cell line must contain a gag gene to express gag protein, a pol gene to express the pol protein, a env gene to express the envelope protein and a rev gene to express the rev protein to bind to the rev-response element (RRE) on transcribed vector genome RNA containing the transgene to facilitate nuclear export for packaging into vector particles at cell surface.

In addition, some lentiviral packaging cell lines contain the tat gene to express tat accessory protein to enhance transcription. However, as current state-of-the-art lentiviral vectors are tat-independent and pseudotyped with heterologous envelopes, the only HIV genes needed for production are gag-pol and rev. In most cases, production of lentiviral vectors has been by transient transfection of 293T cells. Typically these vectors are pseudotyped with the VSV-G envelope, which has a broad tropism and is relatively stable. Transient transfection enables the production of high titers of lentiviral vectors. However, there are a number of limitations. These included a short period of high titer virus production that only lasts a few days and variability between titers in different batches of lentiviral vector. Additionally, there is a possibility of recombination between co-transfected plasmids, compromising the safety of the batches of virus produced. These factors make the stringent safety characterisation and scale up required for good manufacturing practice (GMP) challenging. Aside from these limitations, producing lentiviral vectors by transient transfection is expensive, and unless a more effective means of production is developed, the application of lentiviral vectors to the clinic is likely to be confined to the treatment of diseases with small numbers of patients and therefore low amounts of vector. For applications involving larger numbers of patients, for example β thalassaemia or applications involving direct vector injection such as vaccination, packaging cell lines stably expressing lentiviral vectors would provide a more efficient means of production. This would enable reproducible safety and efficacy batch characteristics, as well as opening new therapeutic options, such as injection of producer cells into patients, allowing long-term in-vivo therapeutic vector production.

There have been a number of challenges in making lentiviral packaging cell lines. Briefly, it has not been possible to achieve sufficient HIV gag-pol expression by stable transfection, which is thought to be a result of toxicity. Furthermore, the envelope most used to pseudotype lentiviral vectors, VSV-G, is also too toxic for stable expression in lentiviral packaging cell lines. Therefore many attempts to make lentiviral packaging cell lines have been inducible, most commonly using tetracycline-regulated promoters to control expression of HIV gag-pol, rev and VSV-G (3, 5, 6, 9, 10, 14, 18). Although an inducible cell line has been developed for clinical use for EIAV vectors (15, 16), none of the published reports of tetracycline regulated inducible packaging cell lines for HIV-based lentiviral vectors have reached clinical trials. The reasons for this involve low titers of stably transfected self-inactivating (SIN) lentiviral vectors, a relatively short period of vector production after induction and difficulties in scale-up.

A stable lentiviral vector packaging cell line, STAR, was previously developed through expressing codon-optimised HIV gag-pol, rev and tat from gammaretroviral vectors, with internal CMV promoters driving expression of the packaging components. Retroviral envelopes (including amphotropic MLV or RD114) were then expressed by stable transfection. Full LTR or SIN lentiviral vectors were introduced by transduction or stable transfection respectively (7). Transduction of STAR cells with full LTR lentiviral vectors led to titers of over $10^7$ infectious units per ml, that were sustained for over 140 days in culture. Stable transfection of a SIN lentiviral vector led to lower titers in producer clones, but most of these were still over $10^5$ infectious units per ml.

Based on calculations on the amount of lentiviral vector required for clinical trials, it is assumed that a packaging cell line preferably requires a titer of at least $10^5$ infectious units per ml to be useful for producing lentiviral vectors for clinical trials. Thus, it is clear that STAR cells make a sufficient titer (even after stable transfection of a SIN lentiviral vector).

The construction of these STAR cells did provide important proof of principle that a stable lentiviral vector packaging cell line was achievable. However, there were a number of issues to be addressed before this work could be translated into clinical application. The cell line was constructed using an MLV vector with wild-type LTRs. Therefore, cross packaging of this vector resulted in HIV gag-pol into virions, which was transferred to cells transduced with vector. Furthermore, the 293T cells used were untraceable and therefore did not meet good manufacturing practice (GMP) guidelines. See the world wide web at ec.europa.eu/health/documents/eudralex/vol-4/index en.htm.

SUMMARY OF THE INVENTION

The inventors have appreciated a need for a lentiviral packaging cell line suitable for clinical use, and in particular, one that is constructed so as to meet GMP guidelines.

The present inventors have solved this need by producing a lentiviral packaging cell line capable of producing a sufficient titer of lentiviral vector required for use in clinical trials and at the same time overcoming previous safety concerns. They have further developed a quick and reproducible way of measuring the expression of the lentiviral vector packaging components.

However, in carrying out this work, the inventors have appreciated that the materials and methods of the invention may also facilitate high level expression of other proteins e.g. non-viral proteins of interest. Accordingly, while the invention is predominantly directed to the production of high titer lentiviral particles, it will be immediately apparent to the reader that the materials and methods described herein can be adapted for the high level expression of proteins in general.

Accordingly, at its most general, the present invention provides materials and methods for expressing proteins, particularly viral proteins, by integrating the coding sequences for these proteins into high-expressing target sites on the cell chromosome. This is achieved by marking or tagging a cell chromosome locus that favours high-level expression of exogenous genes with an integrated exogenous nucleic construct (the tagging construct), which comprises a first and a second recombinase target site. Between these recombinase target sites is a target construct which may comprises a selectable marker gene operably linked to a promoter. The promoter may be part of the target construct or upstream of the first recombinase target site. By using recombinase-mediated exchange, the target construct may be replaced by sequence encoding a protein of interest. Accordingly, the sequence encoding the protein of interest will be integrated into the cell genome in an optimum position for high level and stable expression. This coding sequence may be operably linked to its own promoter or may use the promoter of the original tagging construct that is position upstream of the first recombination target site.

Following integration of the tagging construct into the cell genome, e.g. by standard techniques such as transfection, transduction and transgenesis, a clone may be selected on the basis of the selectable marker which demonstrates high level expression.

Thus, the invention provides materials such as tagging constructs for marking the cell chromosome at a locus that favours high-level expression of exogenous genes ready for recombinase-mediated cassette exchange with sequence encoding the protein of interest; target cells with said tagging construct already integrated into the cell genome, and cells (producer cells) capable of high level expression of the protein of interest following successful recombinase-mediated cassette exchange. These materials along with methods for their production or use are described in more detail below.

In a first aspect of the invention, there is provided a method for producing a cell capable of expressing one or more proteins of interest, comprising the steps of
   (i) providing a cell comprising an exogenous tagging construct integrated into the cell genome, said tagging construct comprising a first and a second recombinase target site positioned so as to define a target construct between them;
   (ii) introducing into said cell an expression cassette comprising coding sequence or one or more proteins of interest, said coding sequence having a recombinase target site at both the 5' and 3' ends; and
   (iii) propagating the cell for recombinase-mediated exchange between the expression cassette and the target construct at their respective recombinase target sites wherein the expression cassette replaces the target construct contained in the integrated construct; and
   (iv) selecting the cell capable of expressing the one or more proteins of interest.

As mentioned above, the invention will now be illustrated with respect to the expression of viral proteins, e.g. gag and pol. However, it will be immediately apparent to the reader that the embodiments described below will be equally applicable to the expression of other proteins.

In accordance with the further aspects below, the invention provides a method for producing a packaging cell line (and isolated clones therefrom) which is capable of producing high titers (e.g. of at least $10^4$ infectious units per ml) after transient transfection of the viral vector. Also provided is a pre-packaging cell line capable of stably expressing gag and pol; packaging constructs used in assembling the cell line; and vector-producer cells derived from the packaging cell line.

The invention is illustrated with particular attention to lentivirus based packaging constructs that can be used to produce a stable packaging cell line and producer cells. The inventors have determined that by providing a target cell with a provirus (tagging construct) already optimally integrated within its genome they are able to insert the required gag and pol coding sequences and at the same time remove any undesirable elements of the provirus. The target cell is then able to express gag and pol proteins and, once other required elements such as env and rev are present, a packaging cell line is produced which is capable of high titer production of viral particles without the presence of undesirable packaging elements from the provirus.

Accordingly, and in line with the first aspect provided above, there is provided a method for producing a cell capable of expressing lentiviral gag and pol proteins, comprising the steps of
   (i) providing a cell comprising an integrated retroviral provirus having a recombinase target site between the U3 and R-region in both the 5' and 3' LTR thereby defining a target construct;
   (ii) introducing into said cell an expression cassette comprising a lentiviral gag and pol coding sequence and having a recombinase target site at both the 5' and 3' ends; and
   (iii) maintaining the cell in an environment suitable for recombinase-mediated cassette exchange between the expression cassette and the target construct at their respective recombinase target sites wherein the expression cassette replaces the target construct contained in the provirus between 5' U3 and the 3' R region; and
   (iv) selecting the cell capable of expressing gag and pol proteins.

The gag and pol coding sequences may be provided as separate gag and pol coding sequences under the control of the same or independent promoters, or, more preferably, they are provided as a gag-pol coding sequence in the wild type configuration with frame shift between gag and pol ORFs. Most preferably, the gag-pol construct is codon-optimised using standard methods available in the art.

By way of example, the inventors have used HIV derived gag-pol, but the invention allows the use of a variety of gag-pol constructs derived from other viruses to be inserted at the same sites provided by the integrated provirus In a preferred embodiment of the invention, the gag-pol construct contains a mutation which results in a histidine to glutamine change at amino acid 87 (H87Q) in the capsid protein. This H87Q mutation provides increased resistance to human and non-human primate restriction factors and therefore allows any expressed lentiviral vector to be used effectively in these hosts and particularly to be used in primate preclinical studies.

The method of the invention uses a recombinase mediated exchange to replace the provirus target construct with the transgene (gag-pol) of the expression cassette. Many site-specific recombinases are known and their target sites can be incorporated into the provirus or expression cassette so that the exchange can take place. The inventors' preferred choice is Cre-Lox recombination. Cre-Lox recombination involves targeting a specific site and splicing it using the enzyme Cre-recombinase. LoxP is a site consisting of 34 base pairs, for example:—

ATAACTTCGTATA-ATGTATGC-TATACGAAGTTAT

In a preferred embodiment, directionality of recombination is ensured by using a mutant recombinase target site (e.g. LoxP site with mutation in the left inverted repeat) in the integrated provirus and the recombinase target site in the expression cassette. For example:—

5'-TACCGTTCGTATA-ATGTATGC-TATACGAAGTTAT 3'

To get a "double mutant" at the 5' recombinase target site after recombinase-mediated cassette exchange, a LoxP site with a mutation in the right inverted repeat in the expression cassette construct (e.g. see FIG. 3) may be used.

By way of example, the sequence may be

ATAACTTCGTATAATGTATGCTATACGAACGGTA

In an alternative embodiment, a right inverted repeat mutant LoxP site may be provided in the targeting construct and a left inverted repeat mutant LoxP site may be provided in the expression cassette. This would result in a double mutant at the 3' recombinase target site after recombinase-mediated cassette exchange.

Thus, following recombinase mediated exchange, the integrated spliced construct will contain a 5' double mutant recombinase targeting site and a wild type 3' recombinase site (see FIG. 3) which means that they cannot recombine.

The method according to the first aspect may further comprise the step of selecting a cell having a provirus successfully integrated into its genome. This requires the provirus to express a selectable marker such as an antibiotic resistance gene. This selectable marker is preferably operably linked to a promoter. Selectable markers include any genes that are able to confer a selectable phenotype. Such selectable markers include kanamycin, neomycin, puromycin, hygromycin, Dihydrofolate reductase (DHFR), Gln synthetase, green fluorescent protein (GFP) or adenosine deaminase (ADA).

By way of example, the inventors used a hygromycin and enhanced GFP (eGFP) fusion protein as selectable maker operably linked to a CMV promoter. The cells were selected in hygromycin and tested for fluorescent intensity that was stable over a number (e.g. 50) of passages. A single vector copy per cell was determined by standard and well known procedures such as quantitative PCR (qPCR).

In a preferred embodiment, the expression cassette further comprises a promoterless selectable marker, e.g. an antibiotic resistance gene. This allows the method to further comprise a second selecting step following the recombinase-mediated exchange of the target construct and the expression cassette. The successful recombination event will result in the expression of the selectable marker which will now be under the control of the upstream 5' U3. In this embodiment, it is preferable that the gag and pol coding sequence is operably linked to a promoter present in the expression cassette.

In accordance with this aspect of the invention, the method may further comprise producing a packaging cell by introducing into the target cell coding sequence capable of expressing rev and env. These genes are preferably introduced using standard techniques such as plasmids comprising expression cassettes. An expression cassette refers to a nucleic acid assembly that is capable of directing the expression of a sequence of interest, in this case an env and/or rev gene. The expression cassette therefore preferably also includes a promoter which is operably linked to the sequence of interest. The expression vector may also comprise a polyadenylation sequence, enhancers, termination sequences and other desired sequences which enable the sequence of interest to be expressed in the host cell. The expression cassette may be part of a plasmid.

The expression vector capable of expressing the gene of interest e.g. env and/or rev, may be introduced into the cell using standard methods such as lipid-mediated transfection, transfection using calcium phosphate, gene gun etc, liposomes, immunoliposomes, electroporation etc.

In a preferred embodiment the env gene is derived from endogenous feline virus, RD114. Other envelope coding sequence may be derived from gamma retroviruses including gibbon ape leukemia virus (GALV) and murine leukemia virus (MLV) and non-gamma retroviruses including avian leucosis virus, foamy virus, measles virus, Ross River virus, rabies virus, baculoviruses, and vesicular stomatitis virus (VSV). VSV-env is capable of conferring a broad host range on the recombinant virus although the inventors have found it too toxic for stable expression in lentiviral packaging cell lines.

The env gene is preferably operable linked to a promoter. The expression cassettes may also include selectable markers also operably linked to the promoter.

Further, in order to provide a producer cell, the method may further comprises introducing a replication-defective lentiviral vector into the packaging cell, said lentiviral vector comprises a 5'LTR, a 3'LTR and a suitable packaging signal. In a preferred embodiment, the replication-defective lentiviral vector is SIN-pHV (see Materials and Methods section below) which may be constructed by cloning the SIN lentiviral LTR from UCOE-gamma-C (Zhang F, et al. (2007). *Blood* 110: 1448-1457 incorporated herein by reference) into pHV (Ref 7) in place of the wild type lentiviral LTR. The plasmid containing the replication-defective lentiviral vector may also comprise a selectable marker in order to select clones from cell cultures which are capable of producing a high titre of virus.

The replication-defective lentiviral vector may comprise a heterologous gene capable of expressing a protein of interest, e.g. a therapeutic protein.

The producer cell will be capable of producing lentiviral-based particles which may contain heterologous (e.g. non-lentiviral) genes such as therapeutic or marker genes.

The method may further comprise harvesting viral supernatants using standard techniques such as filtration of supernatants at appropriate time points after transfection and clonal or bulk drug selection. The viral titer is determined by infection of suitable cells with the viral supernatant.

In a preferred embodiment, the producer cell is capable of producing lentiviral virus titre of at least $10^4$ infectious units per ml or at least $10^5$ infectious units per ml.

Virions or virus particles produced by the producer cell are capable of introducing a nucleic acid sequence (e.g. a transgene) into a cell through a viral entry mechanism. Retroviruses are capable of reverse transcribing its genetic material into DNA and incorporating this genetic material into the target cell's genome following infection.

However, it may be preferably that the transgenic DNA is not incorporated into the target cell's genome (e.g. a patient's cell). In this situation, it is possible to use a pol sequence in which the integrase gene is mutated. In this way the transgenes introduced by the lentiviral vector to the host cell are turned into DNA but are not integrated into the cell's chromosomes. Please see Nonintegrating lentivector vaccines stimulate prolonged T-cell and antibody responses and are effective in tumor therapy. Karwacz K, Mukherjee S, Apolonia L, Blundell M P, Bouma G, Escors D, Collins M K, Thrasher A J. J. Virol. 2009 April; 83(7):3094-103.; and Stable gene transfer to muscle using non-integrating lentiviral vectors. Apolonia L, Waddington S N, Fernandes C, Ward N J, Bouma G, Blundell M P, Thrasher A J, Collins M K, Philpott N J. Mol Ther. 2007 November; 15(11):1947-54; both of which are incorporated herein by reference.

In a second aspect of the invention, there is provided a method of producing a cell comprising an integrated retroviral provirus, said method comprising
(i) introducing into said cell a retroviral vector encoding a selectable marker and having a recombinase target site positioned between the U3 and R-region; and
(ii) selecting a cell by virtue of expression of the selectable marker, wherein expression of the selectable marker is indicative of said retroviral vector being integrated into the genome of the cell thereby producing an integrated provirus having a recombinase target site between the U3 and R-region in both 5' and 3' LTR.

In a preferred embodiment, the recombinase target site is modified to ensure directionality of the inserted coding sequence. For example, if the recombinase target site is LoxP, it may contain a mutation in one of the inverted repeats so that the construct after the recombinase-mediated cassette exchange contains a 5' double mutant recombinase targeting site and a wild type 3' recombinase site.

The retroviral vector is preferably a murine leukemia virus (MLV). MLV vectors show a strong bias in favour of integration in the genome near transcription start sites. Accordingly, use of this retroviral vector allows the provirus to be integrated into the cell chromosome locus that favours high-level expression of exogenous genes. Other retroviral vectors which may be used include human immunodeficiency virus (HIV), equine infectious anaemia virus (EIAV), Rous sarcoma Virus (RSV) and avian sarcoma-leukosis virus (ASLV).

The method according to the second aspect of the invention may further comprise generation of the retroviral vector (e.g. MLV retroviral vector). Generation of the retroviral vector may be achieved by standard methods known in the art such as introducing into a cell nucleic acid sequence capable of expression gag, pol and env proteins, along with a vector plasmid which includes packaging signals and may include a selectable marker for identifying successful packaged cells.

This retroviral vector may then be introduced into the target cell, e.g. by transduction. The packaged pol protein is then cleaved into the integrase, reverse transcriptase and the protease proteins allowing the viral RNA (including any transgenes, e.g. selectable markers) to be reverse transcribed to full LTR double stranded DNA, and integrated into the target cell genome for stable transgene expression. Assuming the transgene includes a selectable marker such as an antibiotic resistance gene, this allows those target cells with successful integrated provirus may be selected when maintained in the presence of said antibiotic.

Retroviral vectors preferably include recombinant retroviral vectors derived from retrovirus such as those listed above.

Any suitable target cell may be used. The inventors have used traceable 293T cells (see Materials and Methods section below). However, where it is intended to generate a producer cell line from the target cell (see below for further details) and that this producer cell be used in a method of gene therapy in a subject, it may be preferably to use a cell obtained from that subject.

In a third aspect of the present invention, there is provided a tagging construct for integration into a target cell in order to mark the cell genome for insertion of a protein of interest for high level expression. This tagging construct comprises a first and a second recombinase target site. To facilitate screening for successful integration into a target cell, the tagging construct preferably additionally comprises a selectable marker positioned between the first and second recombinase target sites and operably linked to a promoter.

In a preferred embodiment, the tagging construct comprises a retroviral vector having a recombinase target site between the U3 and R-region in the 3' LTR. Following integration into the target cell, the recombinase target site will be replicated in the 5' LTR.

Further, the invention provides a target cell for use in the preparation of a stable pre-packaging cell line, said target cell comprising an integrated retroviral provirus having a recombinase target site positioned between the U3 and R-region in both the 5' and 3' LTR thereby defining a target construct.

The target construct preferably comprises a selectable marker gene operably linked to a promoter thereby allowing target cells to be selected which contain an integrated single copy of the provirus. Preferably the target cell is a traceable 293FT cell.

The invention further provides an expression cassette comprising a lentiviral gag and pol coding sequence and having a recombinase target site at both the 5' and 3' ends. The expression cassette may also contain a promoterless selectable marker upstream of the lentiviral gag and pol coding sequence which, when inserted will be expressed under the control of the provirus 5' LTR. In this embodiment, the gag and pol coding sequence is operably linked to a promoter, e.g. CMV promoter. The lentiviral gag and pol gene are preferably derived from HIV. In a preferred embodiment, the expression cassette comprises an HIV gag-pol construct. More preferably the gag-pol construct contains a mutation which results in a histidine to glutamine change at amino acid 87 (H87Q) in the capsid protein.

In this context, an expression cassette refers to a recombinant DNA molecule containing a desired coding sequence and appropriate nucleic acid sequences necessary for the expression of the operably linked coding sequence in the target cell. Nucleic acid sequences required for expression in eukaryotic cells usually include promoters, enhancers, and termination and polyadenylation signals. The expression cassette can be removed or inserted into a vector or plasmid as a single unit.

In a fourth aspect, there is provided a pre-packaging cell line comprising an integrated viral nucleic acid assembly capable of expressing lentiviral gag and pol operably linked to the 5' U3. Alternatively the integrated viral nucleic acid assembly may comprise a selectable marker also operably linked to the 5' U3 with the gag and pol genes operably linked to a heterogenous promoter, e.g. CMV promoter.

In a preferred embodiment, the pre-packaging cell is obtainable or obtained from a method according to the invention.

In a further embodiment the lentiviral gag and pol genes are a codon-optimised HIV derived gag-pol construct. In a further preferred embodiment, the HIV gag-pol construct comprises a mutation at H87Q in the HIV capsid protein.

In a fifth aspect there is provided a packaging cell line comprising an integrated viral nucleic acid assembly capable of expressing gag and pol as described above and a further nucleic acid assembly comprising a nucleic acid sequence capable of expressing an env protein. In a preferred embodiment, the env gene is derived from endogenous feline virus, RD114. Preferably, said packaging cell is obtainable or obtained from a method according to the invention.

A packaging cell line is a recombinant cell line containing nucleic acid sequences expressing retroviral Gag, Pol, Env structural proteins. However, because the packaging cell lines lacks the retroviral nucleic acid sequence of the packaging signal, infectious virions cannot be produced.

Accordingly, in a sixth aspect of the invention there is provided a producer cell line which comprises an integrated viral nucleic acid assembly capable of expressing gag and pol operably linked to the 5' U3 or to a heterogenous promoter; a nucleic acid sequence capable of expressing an env protein and a replication-defective lentiviral vector.

In a preferred embodiment, the producer cell is obtainable or obtained from a method according to the invention.

The replication-defective lentiviral vector may comprise a heterologous gene capable of expressing a protein of interest, e.g. a therapeutic protein.

The producer cell produces lentiviral-based particles which may contain heterologous (e.g. non-lentiviral) genes such as therapeutic or marker genes.

In a seventh aspect, there is provided a lentiviral vector particle obtained from the produced cell according to the sixth aspect. A lentiviral vector particle or virion is capable of introducing nucleic acid into a cell. A lentiviral particle is capable of reverse transcribing its genetic material into DNA and incorporating this genetic material into a target cells genome.

In a preferred embodiment, the lentiviral vector particle is obtainable or obtained from a method of the invention.

This lentiviral vector may be used in a method of gene therapy wherein said lentiviral vector is used to introduce a therapeutic gene into a cell in vitro, ex vivo or in vivo.

In an eighth aspect of the invention, there is provided a method of treating a human or non-human subject requiring gene therapy, said method comprising administering to said subject a producer cell in accordance with the sixth aspect of the invention wherein the replication-defective lentiviral vector comprises an expressible therapeutic gene.

In a preferred embodiment, the producer cell is derived from a cell obtained from said subject.

In a ninth aspect of the invention, there is provided a method of treating a human or non-human subject requiring gene therapy comprising administering to said subject a lentiviral vector particle in accordance with the seventh aspect of the invention, said lentiviral vector particle comprising an expressible therapeutic gene.

In a tenth aspect, there is provided a kit for producing a pre-packaging or packaging cell line for use in the production on lentiviral vector particles, the kit comprising one or more of the following (i) a target cell comprising an integrated retroviral provirus having a recombinase target site between the U3 and R-region in both the 5' and 3' LTR thereby defining a target construct; or a tagging construct for integration into the genome of a target cell, said tagging construct comprising a target construct optional encoding a selectable marker, defined by a 5' and a 3' recombinase target site. The kit may also provide materials and methods of introducing the tagging construct into the target cell, e.g. by transfection or transduction.

(ii) an expression cassette comprising a lentiviral gag and pol coding sequence and having a recombinase target site at both the 5' and 3' ends; and optionally (iii) a recombinase.

In still further preferred embodiment, the recombinase target site contains a mutation upstream of the splice site such that, following recombinase-mediated exchange, the integrated splice construct containing the gag and pol coding sequence will contain a 5' double mutant recombinase targeting site and a wild type 3' recombinase site (See FIG. 3) which means that they cannot recombine. It will of course be appreciated that the combination of mutant LoxP is required but that two orientations are possible resulting in either a 5' or 3' double mutant after recombinase-mediated cassette exchange.

The kit may further comprise an expression cassette encoding env and/or an expression cassette encoding rev.

In a preferred embodiment, the gag and pol genes are derived from HIV and may be provided as separate coding sequences or as a gag-pol construct.

In a further preferred embodiment, the HIV gag-pol contains an H87Q mutation in the HIV capsid protein.

In a still further preferred embodiment, the recombinase target site contains a mutation upstream of the splice site such that, following recombinase mediated exchange, the integrated spliced construct containing the gag and pol coding sequence will contain a 5' double mutant recombinase targeting site and a wild type 3' recombinase site (see FIG. 3) which means that they cannot recombine.

The kit may further include instructions for producing the pre-packaging or packaging cell line in accordance with the first aspect of the invention and/or materials such as diluents, buffers, cell culture media etc for carrying out the method.

In all aspects of the invention, preferred lentiviruses include exogenous, non-oncogenic retroviruses such as human immunodeficiency viruses (HIV-1 and HIV-2), simian immunodeficiency viruses (SIVs), equine infectious anemia virus (EIAV), Feline immunodeficiency virus (FIV), bovine immunodeficiency virus (BIV). The skilled person will be aware of other lentiviruses which may be used within the context of the present invention.

Aspects and embodiments of the present invention will now be illustrated, by way of example, with reference to the accompanying figures. Further aspects and embodiments will be apparent to those skilled in the art. All documents mentioned in this text are incorporated herein by reference.

Black horizontal line: detection threshold=$10^2$ IU/ml

Black downward arrows: titres were below detection threshold

BPuH: Blasticidin+Puromycin+Hygromycin

WRH: WinPac-Rdpro-HV

FIG. 16. Optimised WinPac-RDpro-HV titres with and without Spinoculation. 5-fold serial dilutions of VCM collected from cells grown in the presence of BPIPuH were used to transduce $6 \times 10^5$ 293T cells per well of a 12-well plate in a total volume of 0.5 ml at transduction in the presence of 8 μg/ml polybrene. 12 hrs post-transduction, 0.5 ml of fresh complete medium was added. 24 hrs post-transduction, medium was replaced with 2.5 ml of fresh complete medium. 48 hrs post-transduction, cells were harvested, fixed and analysed for GFP expression by FACS.

BPlPuH: Blasticidin+Phleomycin+Puromycin+Hygromycin

WRH: WinPac-Rdpro-HV

FIG. 17. Titre stability during prolonged culture. Clones were kept in culture with and without BPIPuH. VCM was harvested and titrated at ~3 to 4 week intervals.

Figure 18:
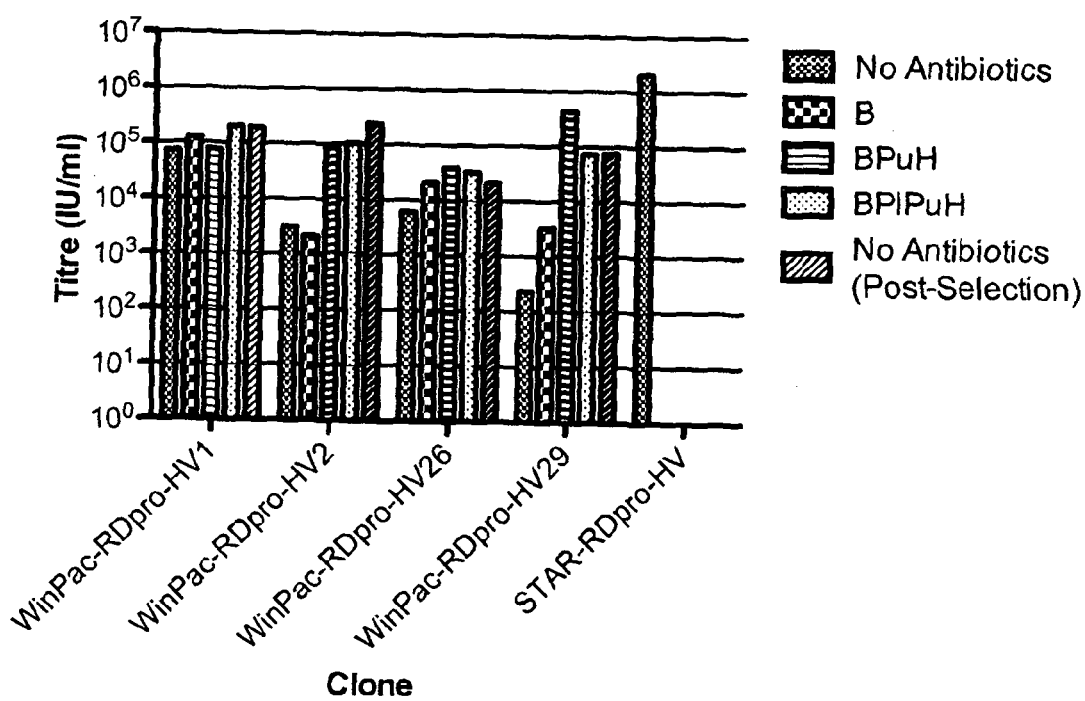

FIG. 18. Antibiotic Selection Rescues WinPac Titres. Clones were thawed out and re-selected in Blasticidin then BPuH followed by BPlPuH. Later, the cells were cultured for a period of ~2 weeks without antibiotics (No, antibiotics, Post-selection). VCM was harvested and titrated at each stage.

BPuH: Blasticidin+Puromycin+Hygromycin

BPlPuH: Blasticidin+Phleomycin+Puromycin+Hygromycin.

Figure 19:
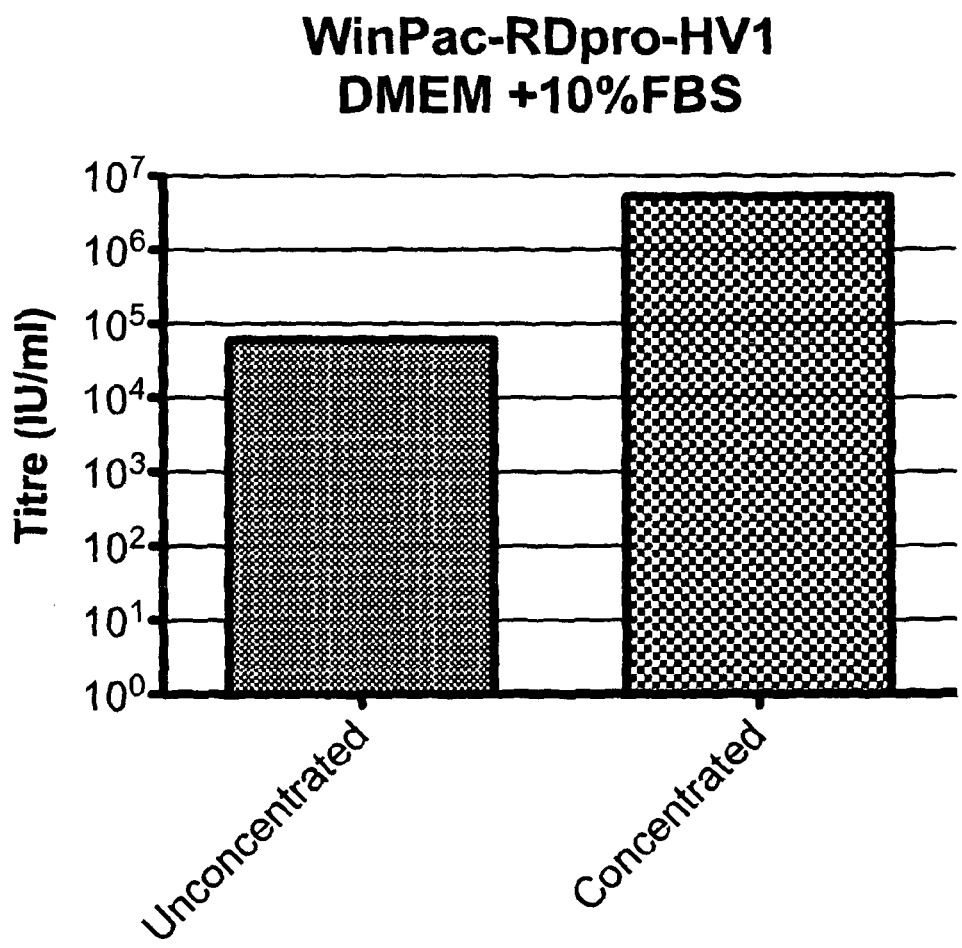

FIG. 19. High-titre vector preparations by ultracentrifugation. Vector-containing medium (DMEM+10% FBS) harvested from one clone (WinPac-RDpro-HV1) was concentrated by ultracentrifugation and resuspended in serum-free medium (X-VIVO10). Titres were determined on 293T cells before and after concentration.

Figure 20:
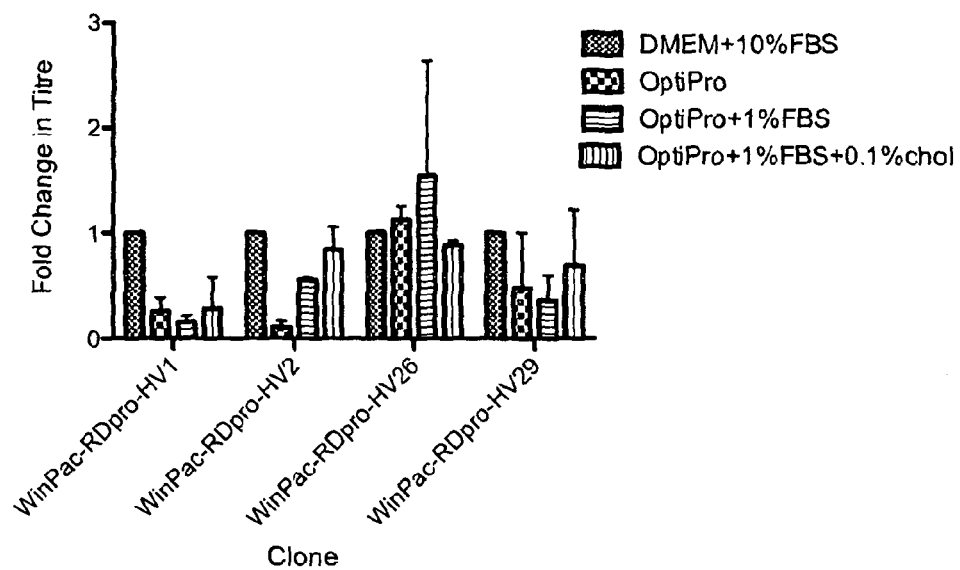

FIG. 20. Reducing and removing serum at Harvest variably affects titre. Vectors were harvested in serum-free medium (OptiPro) as well as medium with reduced serum supplement with and without a well defined cholesterol content.

Figure 21:
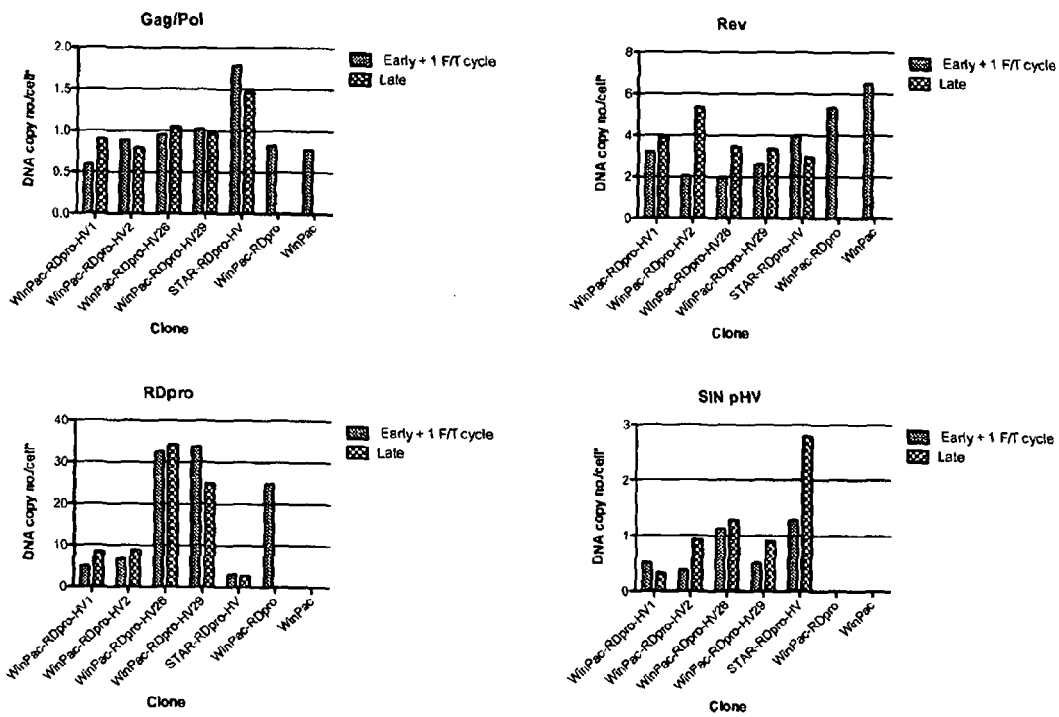

FIG. 21. DMA copy number of packaging components and vector genome in WinPac cells. The DNA copy numbers in packaging cells were determined by RT-Q-PCR for Gag/Pol, Rev, RDpro and SIN pHV at two time points. DNA copy no./cell calculated assuming there are 2 β-actin genes per haploid human genome (Dodemont et al, EMBO J. 1982) and that the 293FT-derived WinPac cells are triploid. STAR-RDpro cells, which are stable high-titre lentiviral packaging cells, were used for comparison.

Figure 22:
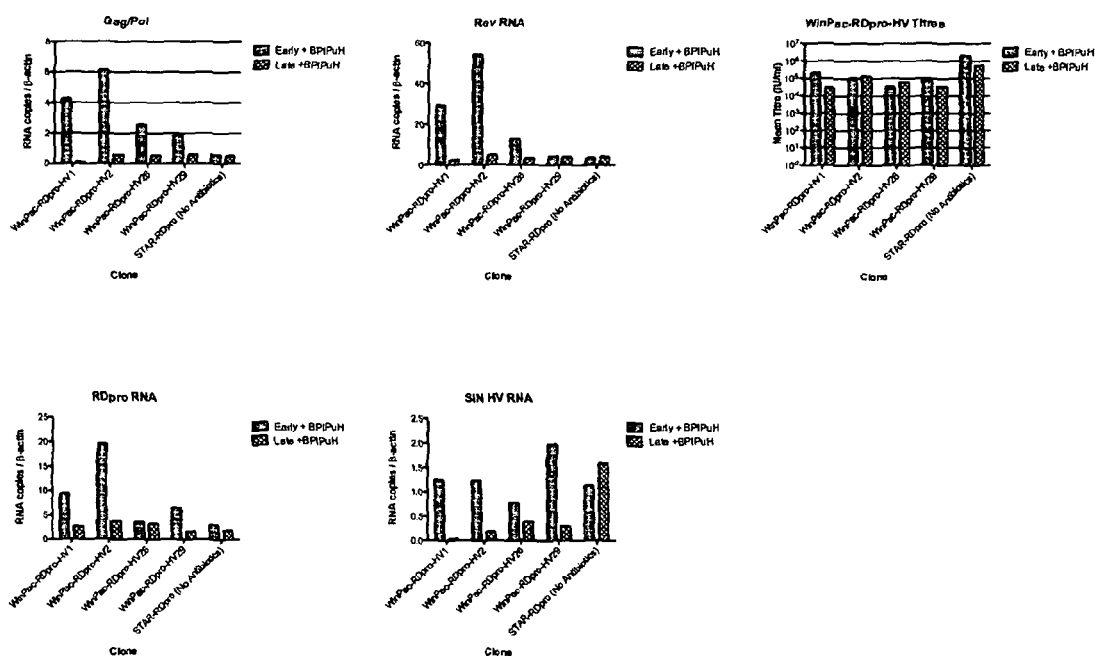

FIG. 22. RNA expression levels of vector components and genome. RNA expression levels were determined by RT-Q-PCR at two time points in the presence and absence of antibiotic selection. The RNA expression levels are normalized to the house-keeping gene (β-actin) RNA expression level. Corresponding titres are also shown.

Figure 23:
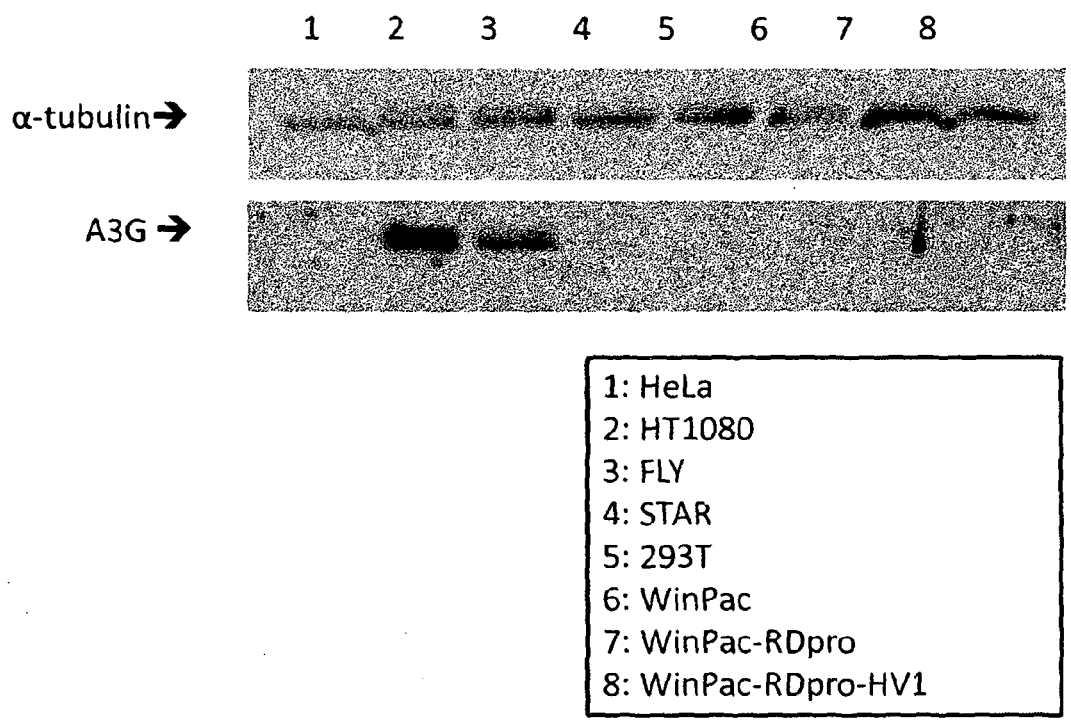

FIG. 23. A3G is undetectable in WinPac cells by western blotting. A3G was undetectable by western blot in the WinPac cells tested at various levels of their development. This was compared to positive (HT1080 and FLY cells) and negative (HeLa cells) controls.

MATERIALS AND METHODS

Cell Culture

Cell lines used were derived from 293FT or STAR cells. 293FT cells are a clean traceable cell line from Genethon; they were derived from 293 cells by stably transfecting the SV40 T-antigen and selecting a fast growing clone. The lot numbers of all reagents added to 293FT cells have been documented. STAR cells were derived from non traceable 293T cells by transduction with MLV vectors encoding a codon optimised HIV gagpol, tat and rev. STAR RD pro cells were made from STAR cells by stable transfection of the RD pro envelope. STAR cells and 293FT cells were grown under the same conditions, i.e. in Dulbecco's Modified Eagle Medium (DMEM) supplemented with 10% Foetal Calf Serum (SAFC Biosciences), 2 mM L-Glutamine, 100 units/ml Penicillin, 100 μg/ml Streptomycin.

Clone 57 cells were made form 293FT cells, and express a codon optimised gagpol cassette (different to gagpol used to make STAR cells). Clone 57 cells were made by transduction of 293FT cells with an MLV based vector, expressing GFP from an internal CMV promoter and containing loxP sites in between U3 and R in the LTRs, to identify a high expressor site based on GFP expression. Recombinase mediated exchange was used to insert the codon optimised gagpol into the high expressor site tagged by the MLV based vector.

Titration of Virus

The amount of virus present in each preparation was quantified as the amount of 'infectious units' per ml. This refers to a functional measure of how many cells you can expect to be transduced for a given volume of virus. Virus was titrated on 293T cells. For 293T, $2 \times 10^5$ cells per well were seeded in a 6 well plate on the day prior to transduction. On the day of transduction, the number of 293T cells in one well was counted for use in titer calculations. 293T cells were transduced with serial dilutions of concentrated or unconcentrated viruses with 5 μg/ml Polybrene (PB) (Sigma) for 5 hours before the medium was changed for fresh medium. The cells were analysed by FACS The number of GFP+ve cells was then used to calculate the number of infectious units added to the cells, and this was multiplied by the dilution factor to give infectious units per ml. The assumption in this calculation is that each GFP+ve cell was transduced successfully by a single virion, so titers were calculated from the dilutions that gave less than 20% GFP+ve cells according to equation below:—

Viral titer (iu/ml)=No. cells exposed to virus×proportion GFP positive cells×dilution factor No. of cells exposed to virus was typically 4×10$^5$, proportion of GFP positive cells was obtained by dividing GFP positive percentage by 100. The dilution factor was calculated by 1000/(amount of virus added (μl)).

Lentiviral Vectors for Packaging Cell Line

This section is concerned with the method involved in production and titration of lentiviral vectors to test titers of prospective packaging cell lines.

Virus Production

All virus production was done in 6 well plates, unless otherwise specified, according to Table 1. On day 0 cells were seeded at between 2×10$^5$ and 1.6×10$^6$ cells per well, as detailed below. On day 1, cells were transfected with missing packaging components and vector. For each well, 25 μl Optimem (Gibco) was added to a sterile microcentrifuge tube, and 2.25 μl Fugene (Roche) added. A total of 437 ng of DNA was assembled in 437 μl with sterile water (Baxter) and added to the Optimem/Fugene mix, incubated at room temperature for 15 min and then added dropwise to cells. pGEM T easy plasmid was used to make up the DNA to 437 ng when packaging cells were transfected with missing packaging components. In the case of producer cells (containing all packaging components and a vector) nothing was transfected, and the medium was simply changed at day 1, and 2.

TABLE 1

Virus production protocol

| Day | Action |
|---|---|
| 0 | Cells seeded in 6 well plates |
| 1 | Medium changed for 1 ml fresh DMEM (missing packaging components transfected) |
| 2 | Medium changed for 1 ml DMEM |
| 3 | Supernatant collected, filtered through 0.45 m filter and stored at −80° C. |

Titration of Vector

Virus was titrated according to Table 2.

TABLE 2

Virus titration protocol

| Day | Action |
|---|---|
| 0 | 293FT cells seeded at 5 × 10$^4$ cells per well in a 24 well plate |
| 1 | 293FT cells transduced with serial dilution of supernatant |
| 2 | — |
| 3 | Transduced 293FT cells trypsinised and analysed by FACS |

Stable Transfection

Stable expression of Rev and RDPro envelope in 293FT cells was achieved by stable transfection. To achieve stable expression using this technique, DNA containing an antibiotic resistant gene was transfected into clone 57. This DNA can be incorporated into the cell genome if a double stranded DNA break in the genome occurs by non-homologous end joining (NHEJ). Stable integrants can then be selected using the antibiotic for which resistance is conferred by the resistance gene encoded in the transfected DNA.

For this work, the antibiotics; puromycin (Sigma), hygromycin B (Calbiotech), phleomycin (Invivogen) and blasticidin S HCl (Invitrogen) were used to select for stable integration. Puromycin works by terminating the formation of polypeptide chains, by accepting a peptide bond and causing early release of polypeptides from the ribosome. Blasticidin S HCl appears to more directly inhibit the ribosomal peptidyl transferase, and interestingly can inhibit the formation of peptide bonds to puromycin when both antibiotics are present. Hygromycin B also inhibits translation of mRNA by ribosomes, but in contrast to puromycin and blasticidin S HCl, it inhibits translocation of the ribosome.

The antibiotics listed above were used in selection because genes conferring resistance to all of them have been extensively characterised. These genes encode enzymes that inactivate the antibiotics through acetylation (puromycin and blasticidin S HCl), phorphorylation (hygromycin B) or sequestering the antibiotic through binding (phleomycin).

Stable Transfection of Rev in Clone 57 pCEP4 Rev plasmid was digested with EcoRV (Promega) and NruI (Promega). This released a 3.8 kb fragment containing Rev under the control of the CMV promoter and the Hygromycin resistance gene under the control of the pTK promoter, which was extracted from an agarose gel using Gel Extraction Kit (Qiagen). A confluent plate of Clone 57 cells was passaged 1:6 into a 10 cm plate the night before transfection with 1.5 μg of Rev/Hygro fragment using Fugene (Roche) and Optimem (Gibco), after 48 h cells were passaged 1:20 and then 5 serial 3 fold dilutions were made, each dilution was used to seed a 10 cm plate in DMEM with 100 μg/ml Hygromycin B (Calbiotech). Hygromycin B and DMEM were filtered through 0.22 μm filter prior to use.

Stable Transfection of RD Pro in 57R10 Cells

RD pro plasmid was linearised by the restriction endonuclease enzyme Ssp I (Promega) and extracted from an agarose gel using Gel Extraction Kit (Qiagen). A confluent 10 cm plate of 57R10 cells was passaged 1:6 into a 10 cm plate the night before transfection with 2.6 μg linearised RD pro plasmid using Fugene (Roche) and Optimem (Gibco). After 48 h cells were passaged 1:20 and then 5 serial three fold dilutions were made, each dilution was used to seed a 10 cm plate in DMEM with 30 μg/ml Phleomycin (Invivogen).

Stable Co-Transfection of Vector and pSelect Blasti MCS in 57R10E Cells

To stably express vector genomes in the packaging cell lines, vector plasmids were co-transfected with pSelect Blasti MCS (Invivogen), an expression plasmid containing the blasticidin resistance gene, BSr, under the control of the CMV promoter. Vector plasmids were co-transfected at a 10:1 molar ratio to pSelect Blasti MCS. Briefly, cells were passaged 1:6 the day prior to transfection with 1.5 μg pSelect Blasti MCS and a 10 fold molar excess of vector plasmid using Fugene (Roche) and Optimem (Gibco). After 48 h cells were passaged 1:20 and then 5 serial 3 fold dilutions were made, each dilution was used to seed a 10 cm plate in DMEM with 10 μg/ml Blasticidin S HCl (Invitrogen). Blasticidin S HCl and DMEM were filtered through 0.22 μm filter prior to use.

Lentiviral Vectors

To construct SIN PHV, the SIN lentiviral LTR from UCOE-gamma-C [Zhang et al (2007); Blood 110: 1448-1457] was cloned into pHV [See Ref 7] in place of the wild type lentiviral LTR. Briefly, pHV was digested with BamHI (Promega) and Apa I (New England Biolabs). The 2 fragments of DNA resulting from this were separated by electrophoresis on a 1% agarose gel. The ~5.7 kb fragment was extracted and kept as a backbone, the ~2.2 kb band was digested with Sac II and the resulting ~1.2 kb fragment extracted from a 1.5% agarose gel after electrophoresis. The SIN LTR from UCOE-gamma-C was amplified by PCR using KOD polymerase (Novagen) by primers Sac WPRE-F and ApaI UCOE RC. This PCR product was then cut with SacII (Promega) and ApaI (present on either side of SIN LTR). The 1.2 kb fragment of pHV cut with SacII and BamHI and the SIN LTR cut with SacII and ApaI were cloned into the backbone cut with BamHI and ApaI using T4 DNA ligase (Promega) overnight at 4° C.

Gammaretroviral Vectors

CNC-Rev was derived by cloning Rev cDNA into CNC-MCS as described by Ikeda et al (7).

Non-Vector Expression Plasmids

The plasmid pCEP4 Rev was constructed by inserting HIV Rev into pCEP4 Plasmid (Invitrogen) using the Hind III and Xho I restriction endonuclease sites.

RD pro contains the RD114 envelope with a HIV protease cleavage site under the control of an MLV LTR, and the Phleomycin resistance gene under the control of another MLV LTR (7).

pSelect-Blasti-MCS (Invivogen) encodes the Blasticidin resistance gene (BSr) under the control of the CMV promoter.

QPCR on gDNA in 293FT and Packaging Cells

QPCR was used to ascertain the number of a construct (e.g. gag-pol cassette) per cell, using SYBR green (Qiagen). In this case, β actin was quantified (using primers HB actin F and HB actin RC) in parallel to any gene of interest and divided by 2 (two copies genome) to give the number of cells in each reaction. For gag-pol, primers Q-gagpol-F and Q-gagpol-R were designed to anneal at the frameshift region between gag and pol genes, which was identical in sequence in all the HIV-1 gagpol constructs used in this work. For Rev, primers Q-Rev-F and Q-Rev-R were used and for β-actin, HB-actin-F and HB-actin RC. Standards used in all QPCRs were $10^5$, $10^4$, $10^3$, $10^2$, and $10^1$ plasmids/µl; for gag-pol and rev, p8.91 was used as a standard; for β actin, the standards were made by cloning the PCR product from HB actin F and RC into pGEM T easy (Promega).

Q-RT-PCR on 293FT and Packaging Cells

Q-RT-PCR was used to quantify gag-pol, rev, RD 114 envelope, HIV leader and human β actin. SYBR green was used in all reactions. Standards for gag-pol and rev were made from p8.91 and pHV was used for HIV leader standards. For RD 114 envelope, and Human β actin, primers used in Q-RT-PCR were used to amplify their products, which were cloned into pGEM T easy to make standards. The standards used in each QPCR were $10^7$, $10^6$, $10^5$, $10^4$, and $10^3$ plasmids/µl. The primers used in each reaction are shown in the table on PCR primers.

Primers

All primer sequences are written 5'-3'

Q-RT-PCR in Packaging Cell Line

| Target mRNA | Primer Name | Primer Sequence |
|---|---|---|
| Human β actin | HB actin F | TGGACTTCGAGCAAGAGATG |
|  | HB actin RC | GAAGGAAGGCTGGAAGAGTG |
| HIV-1 Gagpol | Q-gagpol-F | AAGAGAGCTTCAGGTTTGGG |
|  | Q-gagpol-RC | TGCCAAAGAGTGATCTGAGG |
| HIV-1 Rev | Q-Rev-F | TGTGCCTCTTCAGCTACCAC |
|  | Q-Rev-R | CAATATTTGAGGGCTTCCCA |
| RD 114 envelope | Q-RD-F | AACTCCCAACAGGAATGGTC |
|  | Q-RD-R | TTAAGTAGGCCGTCTTGCCT |

DETAILED DESCRIPTION

As mentioned above, the inventors appreciated a need for a lentiviral packaging cell line suitable for clinical use. The protocol used in this work needed to address some of the issues that prevented the application of STAR cells for clinical use, and thus the inventors needed to consider how they would construct a lentiviral vector packaging cell line to meet GMP guidelines. This involved the use of a clean, traceable cell line at the start of the protocol, and adaptation of the method of stable expression of the packaging components used to make STAR cells to avoid transfer of HIV gag-pol or rev.

GMP guidelines have been drafted into EU legislation and implemented in the UK by the Medicines and Healthcare products Regulatory Agency (MHRA). These guidelines provide a standard that needs to be attained in producing active agents for medicinal use in patients. As parts of these guidelines involve defining the manufacturing process, they can only fully meet these once one has developed a successful lentiviral packaging cell line. Therefore, the inventors conducted their work in a manner that would ensure that the cell line used was still clean and traceable, but with a view to adapting any successful packaging cell lines to meet GMP guidelines at a later stage. On a practical level, this involved conducting all cell culture in a dedicated cell culture hood and incubator, which were kept separate from other cells. Additionally, all the lot numbers of reagent used were recorded, as well as details of all cell culture carried out, to ensure traceability.

As a first point, to address the safety concern of HIV gag-pol or rev transfer, the inventors avoided the use of gammaretroviral vectors with full LTRs. This was because STAR cells were thought to package HIV gag-pol due to the expression of an RNA transcript from the MLV LTR encompassing the MLV packaging signal and HIV gag-pol.

Previously, two separate approaches were taken to develop a lentiviral packaging cell line. In both, 293FT cells were used, a clean traceable cell line from Genethon. These cells were derived from 293 cells, and transfected with the SV40 T-antigen.

Example 1

293FT cells were transduced with a gammaretroviral vector encoding HIV gag-pol. The gammaretroviral vector was similar to that used in STAR cells apart from the LTR, where an enhancer deletion made the vector self-inactivating (SIN). A clone (clone 23) with a single vector integration site, producing the highest level of gag-pol as measured by p24 ELISA, was then transfected with a plasmid, expressing rev under the control of the CMV promoter and the hygromycin resistance gene under the herpes simplex virus thymidine kinase (TK) promoter, and clones with stable integrations were selected using hygromycin. Rev expression was checked by western blot and a clone (clone 6) was chosen for the next step where a plasmid containing the RD114 envelope with an MLV cytoplasmic tail (RD+) was transfected and clones with stable integrations selected using phleomycin. Expression of RD+ was assessed by western blot and one clone (clone F) was chosen for the next stage.

The inventors then worked on clone 23, clone 6 and clone F to test whether clone F could be stably transfected with a SIN lentiviral vector to make a sufficient titer for use in clinical trials.

To assess the function of each packaging component, the titer of clone 23, clone 6 and clone F was measured after transfection of the missing packaging components and a lentiviral vector. In each case, virus was collected 48 h post transfection and titrated on 293FT cells. Clone 23 and clone 6 were compared to STAR cells and 293FT transient transfection. Clone F was compared to STAR RD pro (STAR cells stably expressing RD114 envelope with a HIV protease cleavage site).

Figure 1:
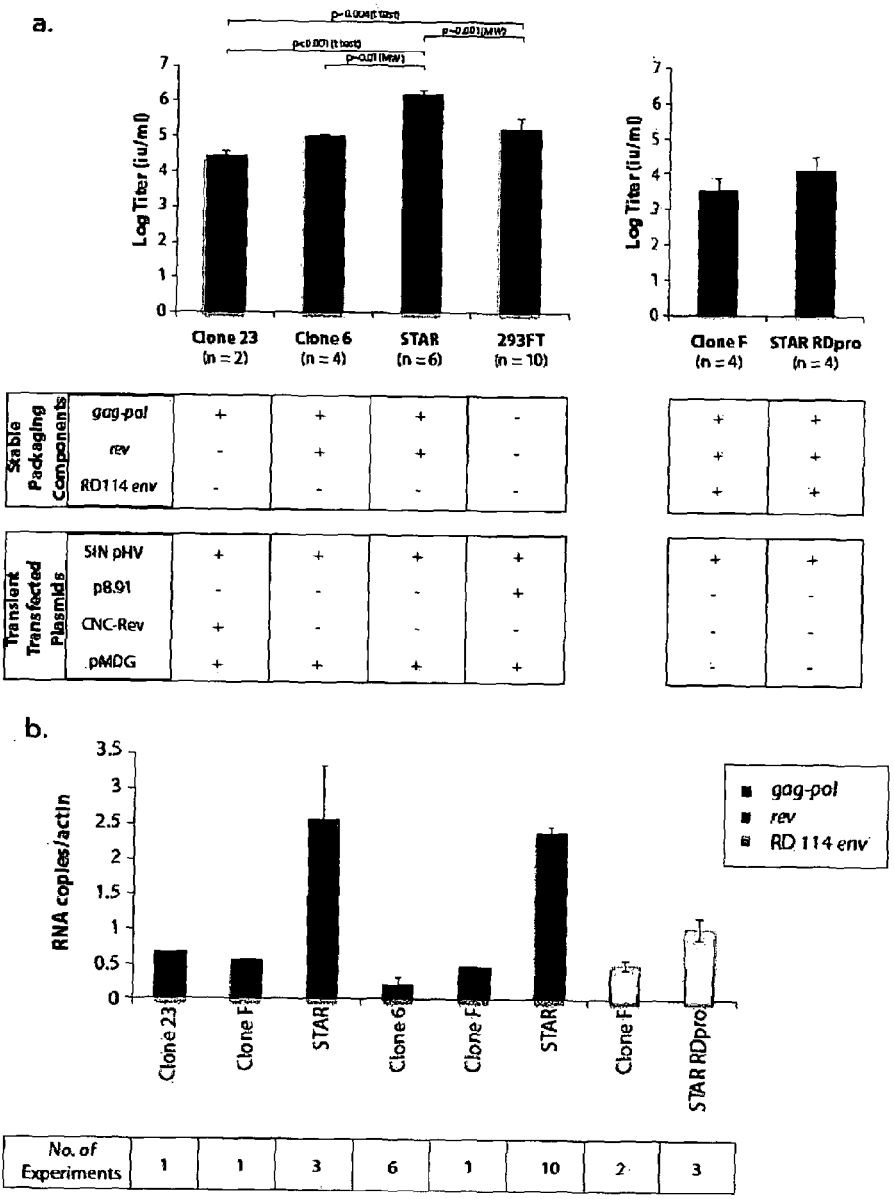
FIG. 1. Testing of the first attempt at a lentiviral vector packaging cell line in 293FT cells. (a.) Titers of each stage of construction of the packaging cells. For each cell line the log titer is shown. The number of replicates is shown underneath the column graphs. Statistically significant results are indicated with p values. If the data passed the normality and equal variance test, the t-test was used; otherwise the Mann Whitney test was used. The statistical test is shown in brackets after the p value (MW, Mann whitney test). The top table underneath the column graphs indicates the stably expressed packaging components in each cell line. Note, Clone F and STAR RD pro were stably transfected with different RD114 constructs. Clone F expresses RD114 with an MLV Env cytoplasmic tail, and STAR RD pro expresses RD114 with an HIV protease cleavage site. The bottom table indicates the transiently transfected plasmids used in each experiment. SIN pHV is a SIN tat independent lentiviral vector, p8.91 expresses gag-pol, tat and rev, CNC-Rev expresses rev only and pMDG expresses VSV-G envelope. Control DNA (pGEM plasmid, Promega) was added to standardise the amount of DNA transfected in each experiment. (b.) RNA expression of each packaging component, measured by Q-RT-PCR. Absolute quantification was used, by linear regression analysis of standards of known amounts of the target DNA sequence. To account for differences in the amount of cDNA added to each reaction, the number of target sequence copies was normalised to the number of actin RNA copies (as measured by Q-RT-PCR) in each sample.

STAR cells transfected with SIN pHV and pseudotyped with VSV-G envelope gave titers of over $10^6$ iu/ml. Transfection of 293FT cells with SIN pHV, p8.91 and pseudotyped with VSV-G envelope gave lower titers than STAR cells, of the order of $10^5$ iu/ml (FIG. 1a). Compared to these controls, clone 23 (stably expressing gag-pol) transfected with rev, VSV-G and SIN pHV had a titer about 10 fold lower than 293FT transient transfection, and about 100 fold lower than STAR (FIG. 1a). Clone 6, however, had a titer comparable to 293FT transient transfection (p=0.288, Mann Whitney test) (FIG. 1a). Interestingly, clone F had a titer that was only about 2 fold lower than STAR RD pro, which was not statistically significant (p=0.072, t-test) (FIG. 1a). In general pseudotyping with RDpro results in lower titers on human cell lines than VSV-G (17), explaining the lower titer of STAR RDpro compared to STAR and clone F compared to clone 6 in FIG. 1a. However as discussed below, RDpro transduces CD34+ cells at least as well as VSV-G and thus would be expected to perform as well in transduction of patients' cells in clinical trials.

To measure the expression of each packaging component, the inventors used Q-RT-PCR on cDNA made from packaging cell RNA. In these studies, STAR cells were chosen as a control, as they have been shown to reproducibly make high titers of lentiviral vectors, and therefore can be assumed to have sufficient expression of all packaging components.

Figure 4:
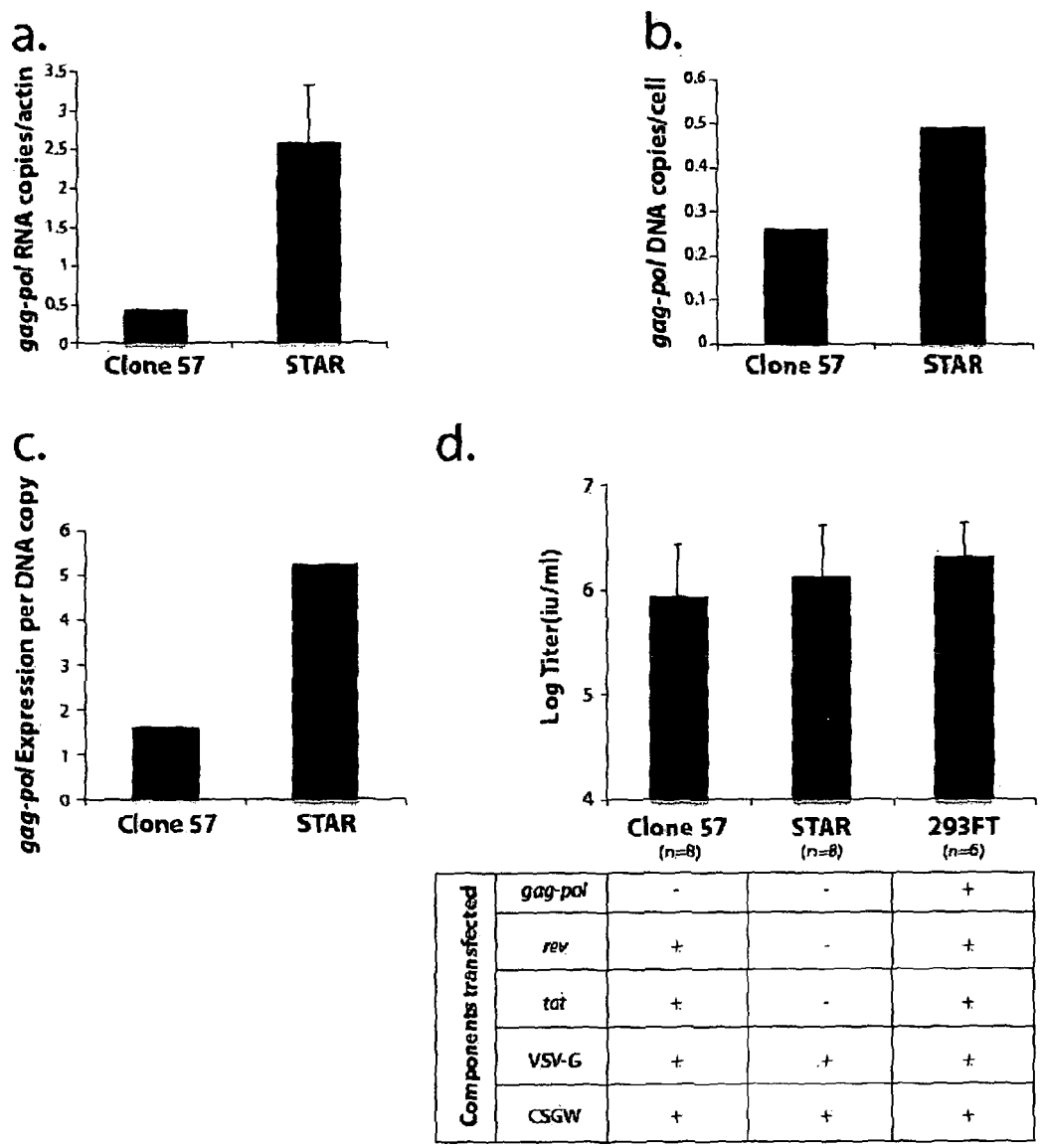
FIG. 4. Testing of Clone 57 function and gag-pol expression. (a.) Q-RT-PCR for gag-pol on cDNA made from RNA extracted from Clone 57 and STAR. The average of 3 Q-RT-PCRs is shown for STAR, and the result of 1 Q-RT-PCR is shown for Clone 57. (b.) Q-PCR for gag-pol on gDNA extracted from clone 57 and STAR. To calculate the number of gag-pol copies per cell, the total number of cells was estimated by quantifying the number of actin copies by QPCR and dividing by 4 (assuming a tetraploid genome). (c.) RNA expression of gag-pol per DNA copy, calculated from the QPCRs for gag-pol on cDNA and gDNA from clone 57 and STAR. (d.) Vector titers produced by clone 57, STAR and 293T. The column graph shows the average log titers of the indicated cell lines and error bars show standard deviation. The number of experiments is shown below each cell line. The bottom table shows the genes that were transiently expressed in each cell line in each experiment. The tat-dependent SIN lentiviral vector CSGW was used for these experiments.

Clone 23 expressed less gag-pol than STAR cells (FIG. 1b), a result that is consistent with the fact that clone 23 has 1 vector copy per cell (G. Santilli unpublished observation) and STAR cells have more than 1 copy per cell by QPCR (FIG. 4b). A lower expression of gag-pol in clone 23 also explains the lower titer than STAR and suggests a suboptimal level of gag-pol in comparison to transient transfection of 293T cells, given the lower titer of clone 23 in comparison to transient transfection.

Clone 6 expressed more than 5 fold less rev than STAR (FIG. 1b). Given that Clone 6 is derived from clone 23 and therefore also expresses less gag-pol than STAR, if rev expression was sub-optimal in clone 6 it would be expected to have a lower titer than clone 23 and STAR. However, although clone 6 has a significantly lower titer than STAR, it does not have a significant difference in titer to clone 23 or 293FT transient transfection. Thus it is possible that STAR expresses more rev than is necessary for vector production, and therefore clone 6 may express sufficient rev for a packaging cell line.

Clone F expressed about 2 fold less RD114 env in comparison to STAR RDpro (FIG. 1b). However, it is unclear if this difference significantly affects titer.

The results in the previous two sections show that clone F expresses sufficient (albeit less than STAR) amounts of gag-pol, rev and RD114 env to support virus production following transient transfection of a SIN lentiviral vector. This data enabled progression to the next step, which was to stably express a vector in clone F.

Clone F was co-transfected with SIN pHV and pSelect Blasti MCS (containing blasticidin resistance gene) at a molar ratio of 10:1. After 48 h, the transfected cells were selected in blasticidin. Clones were screened by fluorescent microscopy to identify GFP positive clones, which were selectively expanded. In total 10 GFP positive clones were obtained, and supernatant from 9 of these was tested for titer. Only one clone (FS9) had a detectable titer. Interestingly, this titer was $10^4$ iu/ml, which is higher than clone F transiently transfected with the same vector. FS9 was grown for 73 days, and periodically the titer was measured. As a control, 293FT cells were grown for the same time course and periodically transfected with SIN pHV, p8.91 and RD pro envelope.

Figure 2:
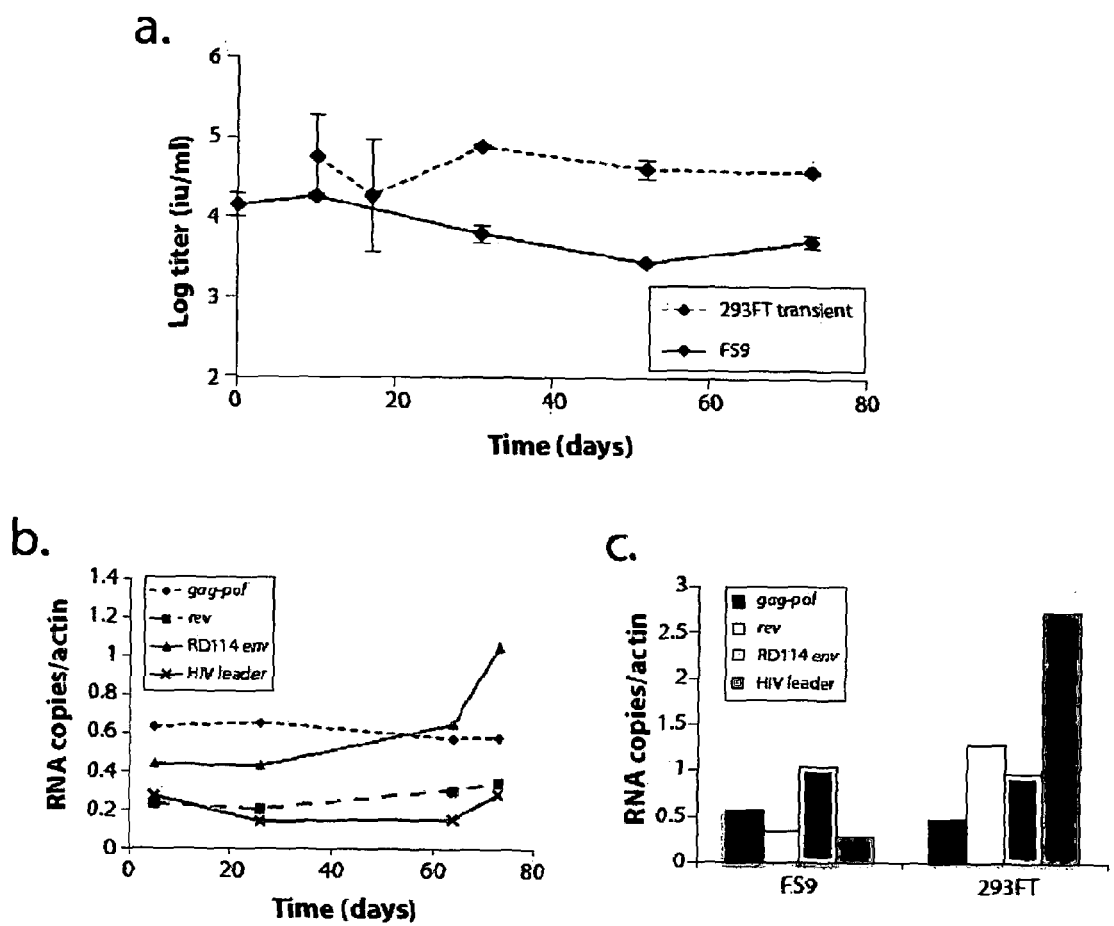
FIG. 2. Analysis of stable producer clone FS9, obtained from stable co-transfection of clone F with SIN PHV and pSelect-Blasti-MCS. (a.) Long term titer. FS9 was cultured for 73 days, and periodically supernatant was taken for titration on 293FT cells. At each of these points, 2 wells of a 6 well plate were seeded and supernatant removed 72 h later. In parallel, 293FT cells were cultured for a similar time and periodically were transiently transfected (in duplicate) with SIN pHV, p8.91 and pMDG to transiently produce vector particles. (b.) At each point where titer was measured for FS9, RNA was extracted from the cells and expression of the packaging components was determined by Q-RT-PCR, normalised to β actin RNA expression. (c.) Expression of each packaging component and SIN pHV vector genome (HIV leader) in FS9 and transient transfected 293FT at 73 days.

293FT fluctuated but only decreased by about 2 fold over 73 days (FIG. 2a) and the expression of SIN pHV and packaging constructs was stable over 73 days (FIG. 2b).

As a control, the amounts of expression of all the packaging components were measured in 293FT cells transiently transfected with SIN pHV, p8.91 and RD pro envelope (virus collected at day 73). Transient transfection seems to result in a similar level of gag-pol expression to FS9. However, transient transfection results in substantially higher expression of rev, envelope and vector than FS9 (FIG. 2c).

In summary, clone F, expressing gag-pol, rev and an RD114 envelope, was found to have substantially lower RNA levels of each of the packaging components compared to STAR. Interestingly, lower expression of packaging components in Clone F did not lower titer significantly in comparison to STAR RDpro, after transient transfection of a lentiviral vector. A stable producer clone (FS9) was then made from clone F by stable transfection of a SIN lentiviral vector. FS9 produced a higher titer than clone F transiently transfected with the same vector.

Example 2

The inventors then attempted to make a lentiviral packaging cell line from 293FT cells. This differed from the first attempt described in Example 1 in the codon optimised HIV gag-pol that was used, as well as the method of HIV gag-pol expression.

Recombinase-mediated cassette exchange (RMCE) was used to stably express HIV gag-pol. In principle, this involved 'tagging' a chromosomal location that was able to support good expression of a GFP cassette and then using cre-recombinase to exchange GFP for HIV gag-pol.

To tag a high expresser site, a mutant loxP site (with a mutation in the left inverted repeat), was cloned into the 3' LTR of a gammaretroviral vector encoding a hygromycin-GFP fusion gene under the control of the CMV promoter (FIG. 3a). 293FT cells were infected at a low MOT and selected in hygromycin to obtain clones with a single copy of the gammaretroviral vector containing a target construct. One of these, clone 2G had a relatively high mean fluorescence intensity (MFI) (FIG. 3b) that was stable over 50 passages and a single vector copy per cell by QPCR, and was thus chosen for the next stage, where GFP was exchanged for gag-pol by RCME. The integration site in clone 2G was cloned by inverse PCR and mapped to the X chromosome in the first intron of midline 1 gene (MID1) in the reverse orientation at nucleotide position 10587225 (Ensembl release 60, November 2010).

Figure 3:
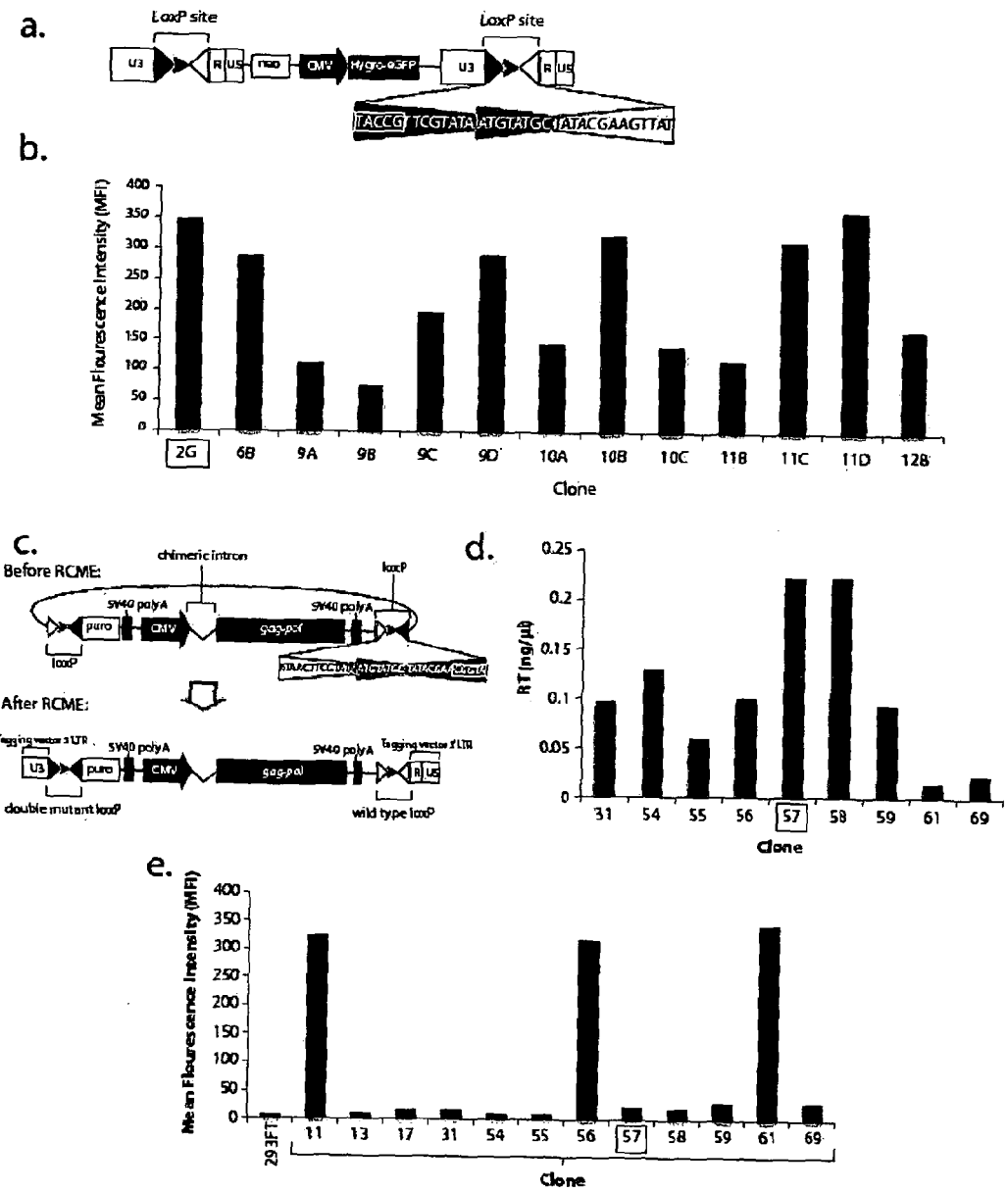
FIG. 3. Expression of HIV gag-pol in 293FT cells by recombinase-mediated cassette exchange (RMCE). (a.) The tagging MLV vector is shown. This has loxP sites in between U3 and R in both LTRs of the integrated vector. The loxP sites contain a mutation in the left inverted repeat (enclosed in a red box). Neo, neomycin resistance gene; CMV, minimal cytomegalovirus promoter; Hygro-eGFP, hygromycin e-GFP fusion gene. (b.) Mean fluorescence intensity (MFI) of hygromycin resistant clones after transduction of 293FT cells with the tagging vector. Clone 2G, which was chosen for the next step is enclosed within a red box. (c.) Schematic of the expression cassette plasmid shown before recombinase-mediated cassette exchange (RCME) on top and after RCME below. The targeting vector has two mutant loxP sites before RCME, both of which have a mutation in the right inverted repeat (enclosed in a red box). HIV gag-pol was under the control of the CMV promoter. A chimeric intron consisting of the splice donor site from the first intron of the human β globin gene, and a branch point and splice acceptor site from the gene for the immunoglobulin heavy chain variable region. RMCE results in excision of the expression cassette construct in tagging vector from 5'R to 3'U3 inclusive, and integration of the targeting construct from the 5' promoter-less puromycin resistance gene (puro) to the 3' SV40 polyA site inclusive. This leads to a double mutant loxP site at the 5' end and a normal wild-type loxP site at the 3' end. (d.) Elisa for reverse transcriptase (RT) on a selection of puromycin resistant clones. Clone 57, enclosed by a red box was chosen for further analysis. (e.) MFI of puromycin resistant clones shows loss of GFP expression in clone 57 (i.e. successful excision of target construct).

An expression cassette plasmid was then made, encoding HIV gag-pol under the control of the CMV promoter. The codon-optimised gag-pol in this plasmid had a histidine to glutamine change at amino acid 87 in HIV capsid, that did not affect titer in human cells (8). Additionally, the codon-usage in this construct substantially differed from the former gag-pol construct which was used in STAR and clone F. Mutant loxP sites (with a mutation in the right inverted repeat) were cloned upstream and downstream of the gag-pol expression cassette. To enable selection of successful recombination events, a promoter-less puromycin resistance gene was cloned downstream of the 5' mutant loxP site. This meant that in a successful recombination, the promoter-less puromycin resistance gene would be placed downstream of the MLV U3 region of the target construct, and thus would be transcribed conferring resistance to puromycin. Importantly, directionality of recombination was ensured by using the mutant loxP sites as after recombination these generate a mutant loxP site and a full wild type loxP site at the tagged genomic location, which cannot recombine (FIG. 3c). Co-transfection of Cre-recombinase and the expression cassette plasmid led to successful recombination in at least two clones, which gained reverse transcriptase (RT) and lost GFP expression (FIGS. 3d and e).

The most promising clone, clone 57, was chosen for further analysis. Expression of HIV gag-pol was confirmed by Q-RT-PCR on cDNA from clone 57 RNA, and was about 4-5 fold lower than STAR cells (FIG. 4a). Clone 57 was confirmed to have less gag-pol DNA copies than STAR, which is consistent with the fact that a lower MOI was used to tag 293FT cells to make clone 2G than was used in transduction of 293T cells to make STAR cells (FIG. 4b). Interestingly, gag-pol RNA expression per integrated DNA copy was also lower in clone 57 than STAR, indicating that the gammaretroviral vectors expressing gag-pol in STAR cells are more efficient than the gag-pol expression cassette in clone 57 (FIG. 4c). Despite a lower HIV gag-pol expression, clone 57 produced a similar titer to STAR and 293FT when transiently transfected with the tat-dependent lentiviral vector, CSGW and the relevant missing packaging components (FIG. 4d). On the basis of these results, clone 57 was determined to express sufficient HIV gag-pol for progression to the next stage, where HIV rev was stably expressed.

Expression of Rev in Clone 57

Figure 5:
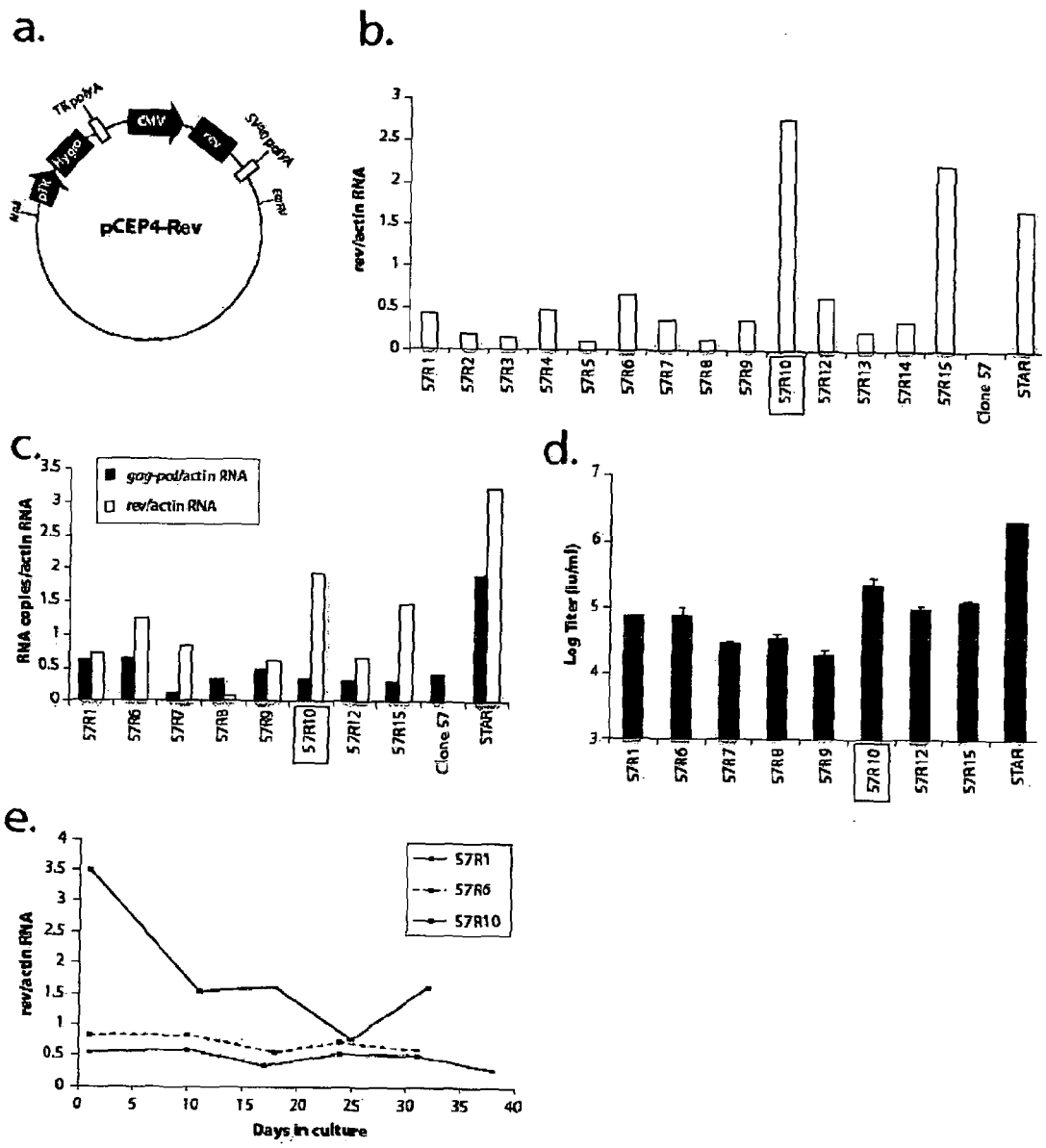
FIG. 5. Stable expression of rev in clone 57. (a.) Plasmid map of pCEP4-Rev. pCEP4-Rev was digested with blunt cutting enzymes NruI and EcoRV, and the fragment containing the hygromycin and rev expression cassettes was stably transfected in clone 57 cells. pTK, Herpes simplex virus thymidine kinase promoter; Hygro, hygromycin B resistance gene; TK polyA, herpes simplex virus thymidine kinase polyA signal; CMV, human cytomegalovirus immediate-early promoter; SV40 polyA, simian virus-40 polyA signal. (b.) Expression of rev RNA in 14 hygromycin resistant clones (57R clones), measured by Q-RT-PCR on cDNA. This measurement was made at the time that the first liquid nitrogen stocks were made for each clone and is noted as day 0. The number of rev copies in each reaction was normalised to the number of actin copies in a parallel Q-RT-PCR. As the Q-RT-PCRs for the clones were carried out in 4 separate reactions, STAR cDNA was used as an internal control in each Q-RT-PCR. The clone chosen for progression to the next stage is enclosed in a red box. (c.) gag-pol and rev RNA expression was measured by Q-RT-PCR in a subset of 57R clones and STAR after 7 days in culture, and normalised to actin RNA expression, measured in a parallel Q-RT-PCR. (d.) Supernatant from 57R clones and STAR was titrated on 293FT cells 48 h after transient transfection of the SIN lentiviral vector, SIN pHV and the VSV-G envelope. Average log vector titers are shown from two experiments for each clone, error bars indicate standard deviation. (e.) Expression of rev in 3 57R clones over 30-35 days, measured by Q-RT-PCR, STAR cDNA was used as an internal control.

The inventors then expressed rev, using the rev expressing plasmid, pCEP4-Rev (FIG. 5a). pCEP4-Rev was digested with two blunt cutting enzymes to release the fragment containing the hygromycin resistance gene and rev expression cassettes. This was transfected into clone 57 and stable integrants were selected using hygromycin B. All of the 14 hygromycin resistant clones (57R clones) that were expanded expressed some rev RNA, as measured by Q-RT-PCR (FIG. 5b).

A subset of the 57R clones were analysed further by measuring expression of gag-pol by Q-RT-PCR and the titer produced after transient transfection of SIN pHV and VSV-G envelope. Most of the clones had maintained some expression of gag-pol (FIG. 5c). The clone expressing the highest level of rev RNA was 57R10, although rev expression decreased about 2 fold in the first 7 days in culture, i.e. between FIGS. 5b and 5c. 57R10 also had the highest titer out of the 57R clones, which was about 10 fold lower than STAR cells (FIG. 5d). Although the level of rev expression in 57R10 fluctuated, it was consistently higher than two other promising clones (57R1 and 57R6) over more than 30 days in culture (FIG. 5e). The decrease in rev expression between days 1 and 10 in culture did not cause a substantial change in transient titer after SIN pHV and VSV-G transfection. Thus 57R10 was chosen for the next step, where an envelope was stably expressed.

Stable Expression of an Envelope in 57R10

Figure 6:
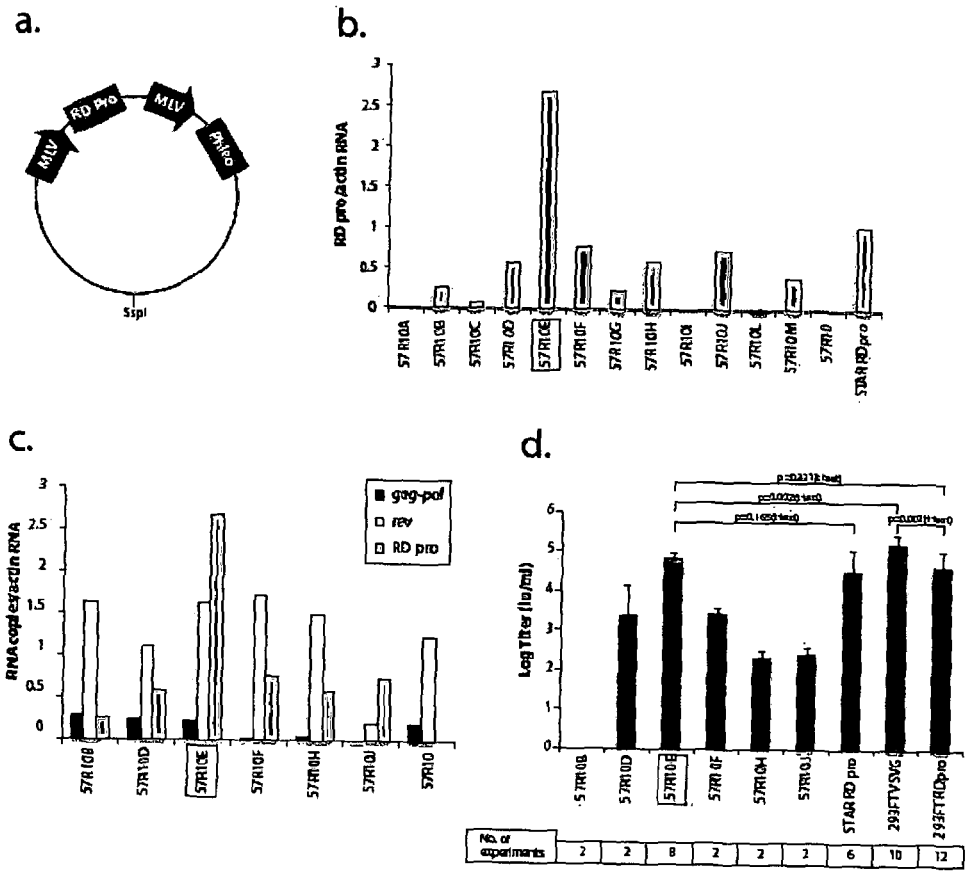
FIG. 6. Stable expression of RD pro envelope in clone 57R10. (a.) plasmid map of RDpro plasmid used in stable transfection. Two MLV LTRs drive expression of RDpro gene and phleomycin resistance gene (phleo). The SspI restriction endonuclease enzyme was used to linearise the plasmid before stable transfection. (b.) Expression of RDpro envelope in 12 phleomycin resistant clones, clone 57R10 and STAR RDpro. (c.) gag-pol and rev RNA was measured in a subset of phleomycin resistant clones, by Q-RT-PCR and normalised to actin RNA copies from a parallel Q-RT-PCR. (d.) Titers of a subset of phleomycin resistant clones and STAR after transient transfection of a SIN lentiviral vector (SIN pHV). As a control, 293FT cells were transfected with p8.91 (encoding gag-pol, rev and tat), SIN pHV and either VSV-G envelope (293FT VSV-G) or RDpro envelope (293FT RDpro). The number of experiments is shown below each clone/cell line. Statistical tests between 57R10E and the controls are shown, only the difference between 57R10E and 293FT VSV-G was significant (p=0.002), the test that was used is shown in brackets. 293FT transfected with VSV-G gave a significantly higher titer than 293FT transiently transfected with RDpro (p=0.002). Clone 57R10E was chosen for progression to the next stage and is enclosed in a red box in (b.), (c.) and (d.).

The envelope stably expressed in 57R10 was a derivative of RD114 env, which has a HIV protease cleavage site in the cytoplasmic tail. The plasmid encoding RDpro contains two promoters derived from an MLV LTR, which drive expression of RDpro and the phleomycin resistance gene (FIG. 6a). 57R10 was transfected with a linearised RDpro plasmid and stable integrants selected using phleomycin. Expression of RDpro varied in the 12 phleomycin resistant clones that were expanded for analysis (FIG. 6b). Many of these clones had also lost expression of rev or gag-pol (FIG. 6c). The clone with the highest expression of RDpro had maintained expression of gag-pol and rev, and also produced the highest titer after transfection with the SIN lentiviral vector, SIN pHV, at around $10^5$ infectious units per ml (FIG. 6d). The titer produced by 57R10E was not significantly different from STAR RDpro transfected with the same vector, or transient transfection of 293FT cells with the RDpro envelope, packaging components and SIN pHV.

Pseudotyping SIN pHV with RDpro envelope decreased titer about 5 fold in comparison to VSV-G in transient transfection in 293FT cells, which was statistically significant (p=0.002, t test). This is consistent with reports of SIV lentiviral vectors pseudotyped with modified RD114 envelope glycoproteins, where the latter had about 5 fold lower titers when titrated on the human cell line TE671. However, lentiviral vectors pseudotyped with RD114 with an MLV cytoplasmic tail had a higher titer than VSV-G pseudotypes, when titrated on peripheral blood CD34+ cells (13). This result has been replicated in HIV-1 lentiviral vectors (4) and RDpro pseudotyped lentiviral vectors produced from STAR cells have also been shown to transduce CD34+ cells efficiently (12). Therefore, stably produced RDpro pseudotyped vectors with comparable titer to transient RDpro pseudotypes in our system would be likely to perform as well as transient VSV-G pseudotypes on CD34+ cells.

Stable Expression of a SIN Lentiviral Vector in 57R10E

To make a producer cell from the packaging clone 57R10E, a lentiviral vector needed to be stably expressed in the packaging cell line. As this packaging cell line was developed for clinical use, the vector needed to be a SIN lentiviral vector. For this purpose the inventors used a previously constructed SIN pHV by cloning the 3' SIN LTR from UCOE-gamma-C in place of the full 3'LTR of pHV. SIN pHV was co-transfected with pSelect Blasti MCS (containing the blasticidin resistance gene—BSr) (FIG. 7a), at a molar ratio of 10:1 and stable integrants were selected using blasticidin.

Figure 7:
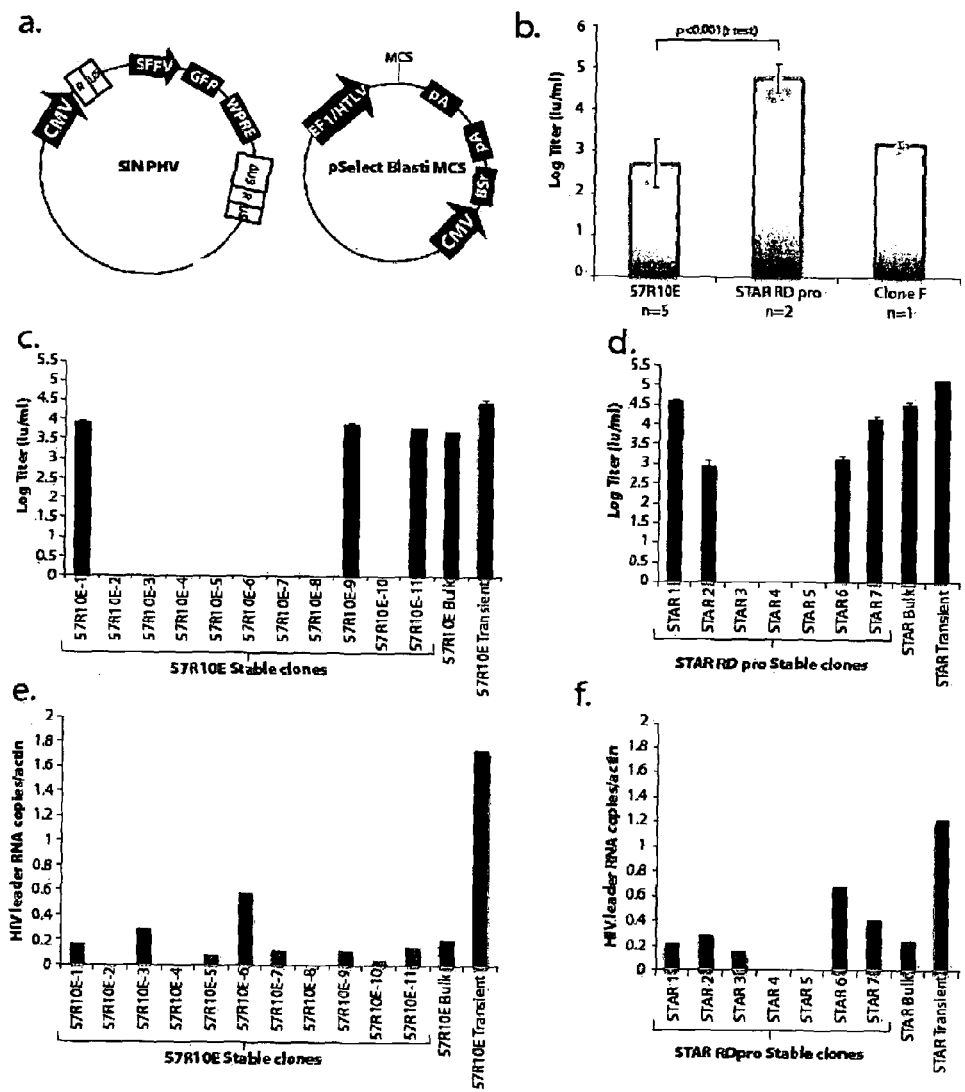
FIG. 7. Stable transfection of 57R10E with the SIN lentiviral vector, SIN pHV. (a.) Plasmid maps for SIN pHV and pSelect-Blasti-MCS (BSr). CMV, human cytomegalovirus immediate-early promoter; SFFV, spleen focus forming virus promoter; GFP, green fluorescent protein; WPRE, woodchuck-post transcriptional regulatory element; EF1/HTLV, a composite promoter of elongation factor-1α (EF-1α) core promoter and human T cell leukaemia virus (HTLV) type 1 R and U5 segments; MCS, multicloning site; pA, polyA site; BSr, blasticidin resistance gene. (b.) Co-transfection of SIN pHV and BSr, followed by selection for stable producer cells in 57R10E, STAR RDpro and Clone F. Average log titers from bulk (i.e. not clonal) blasticidin resistant cultures, error bars indicate standard deviation. The number of independent stable transfections is shown underneath each clone, titers were measured in duplicate for each experiment. (c.) Average titers of GFP positive clones isolated from one bulk culture of 57R10E stably transfected with SIN pHV and BSr (EP clones) (n=2 for each clone). The titer of the bulk culture from which the clones were isolated is shown (labeled as 57R10E Bulk). As a control, the titer of 57R10E transiently transfected with SIN pHV is shown (57R10E transient). (d.) Average titers of GFP positive clones isolated from one STAR bulk culture of STAR RDpro stably transfected with SIN pHV and BSr (n=2 for each clone). The average titer of the bulk culture from which the clones were isolated is shown (labeled as STAR Bulk). The transient titer of STAR RDpro after transfection of SIN pHV and BSr, but before selection in blasticidin is shown (STAR transient). (e.) Q-RT-PCR for HIV leader RNA in EP clones, 57R10E bulk and 57R1DE transiently transfected with SIN pHV. (f.) Q-RT-PCR for HIV leader RNA in STAR clones, STAR bulk, and STAR RDpro transiently transfected with SIN pHV and BSr.

In FIG. 7b, the average titer of 5 stable transfections in 57R10E is shown. In each experiment, supernatant from the heterogenous population of blasticidin resistant clones ('bulk' cultures made up of more than 50 clones) was titrated to give an over-all view on the efficiency of stable transfection. As shown in FIG. 7b, stable transfection of 57R10E resulted in a titer about 100 fold lower than STAR RDpro, and on average about 5 fold lower than stable transfection of clone F. This result was not expected given the equivalence in transient titer of STAR RDpro and 57R10E after SIN pHV transient transfection.

As SIN pHV encodes GFP, the inventors selected GFP positive clones from single bulk cultures of 57R10E and STAR RDpro. 57R10E clones were isolated from a bulk population that yielded 10 fold higher titer than the average 57R10E bulk titer (FIG. 7c). The STAR RDpro clones were isolated from a population with a 2 fold lower titer than the average STAR RDpro bulk titer (FIG. 7d). Therefore, the 57R10E bulk titer used for clonal isolation was only 5-6 fold lower than the STAR RDpro bulk culture used for clonal isolation.

In both 57R10E and STAR RDpro, there was variation in titer between the clones and some clones did not produce a detectable titer. In both 57R10E and STAR RDpro, the clone with the highest titer was about the same as the titer of the bulk population from which the clone was derived. As some clones do not produce any vector particles, it is assumed that there are clones in the bulk population with titers considerably higher than the bulk population. However these clones may be rare and the numbers of clones screened in these experiments (11 for 57R10E and 7 for STAR RDpro) were probably too low to obtain such clones. In any case, as the best clones from STAR RDpro and 57R10E differed about 5 fold in titer, as did the individual bulk cultures from which these clones were derived, the titers of bulk cultures can be considered representative of individual clones.

Expression of transgenes by stable transfection is known to give a highly variable level of expression owing to the random nature of DNA integration. Therefore the inventors considered whether the variability in titer between clones was a result of variation in vector genome expression. To this end, HIV leader expression was quantified by Q-RT-PCR; this did not seem to explain the differences in titer between the 57R10E clones (FIG. 7e). Interestingly, although HIV leader expression was not predictive of titer in STAR RDpro clones, most of the clones that expressed some HIV leader also made a detectable titer (FIG. 7f), in contrast to the 57R10E clones. It is also noteworthy that HIV leader expression in transient transfection was about 2-5 fold higher than stable expression in both 57R10E and STAR RDpro.

In summary, stable transfection of SIN pHV resulted in significantly lower bulk titers in 57R10E compared to STAR RDpro. This difference was also reflected in stable producer clones isolated from bulk cultures. In stable producer clones from both 57R10E and STAR RD pro there was variation in titer, which was not explained by variation in expression of the vector genome.

Packaging Component Expression after Stable Transfection of SIN pHV

To gain further insight into the variation in titer between individual 57R10E and STAR RDpro clones, expression of each packaging component was quantified in all the clones by Q-RT-PCR. In both 57R10E and STAR RDpro clones, where absence of titer occurred in the presence of good HIV leader expression substantial loss in expression of at least one packaging component was demonstrated (FIGS. 8a and b). Interestingly, 57R10E clones on average lost more packaging components per cell than STAR RDpro clones (FIG. 8c).

DNA from a subset of 57R10E clones and all of the STAR RDpro clones was analysed to investigate whether the losses in packaging component expression were due to silencing or DNA loss. The 57R10E clones with a substantial loss in gag-pool RNA expression after stable transfection of SIN pHV had no loss in gag-pol DNA copies/cell. Similar loss of RNA expression but not DNA copies was observed in some STAR RDpro clones (FIG. 9b). However, the 57R10E clones that lost rev RNA expression also lost rev DNA copies/cell. 57R10E clones that had a substantial loss of RDpro RNA lost RDpro DNA as well in one case and maintained it in the other (FIG. 9a). Therefore, silencing seems to be the cause of gag-pol expression loss in 57R10E, however this is not the case with rev expression, where the DNA expression cassette is lost rather than silenced. In RDpro the situation appears to be more complex; although one clone lost the expression cassette and another clone appeared to lose expression through silencing, there is a large difference between the amount of RDpro DNA in 57R10E clones compared to STAR RDpro clones. Many of the 57R10E clones have as much as a 10 fold higher RDpro DNA copy number than any of the STAR RD pro clones, which is not reflected in the RNA levels of RDpro, implying a number of expression defective RDpro copies in 57R10E clones.

As STAR RDpro clones did not lose gag-pol or rev DNA, one can assume that the MLV vectors used to express these constructs allow long term, stable integration. This is supported by the stability of DNA integration of gag-pol in 57R10E, which was integrated by RCME into an MLV provirus. Stable transfection appears to confer less stability in integration than MLV vectors, as shown by the loss of DNA copies of stably integrated rev and RDpro in some cases. Therefore, STAR RDpro only has to contend with silencing of gag-pol and rev, which are present at more than one copy per cell, whereas 57R10E has to contend with silencing of a single gag-pol copy and DNA loss (and probably silencing as well) of rev. Thus STAR RDpro clones appear to have more robust expression of packaging components and thus obtaining high titer producer clones may be more likely after stable transfection of STAR RDpro than 57R10E.

Figure 8:
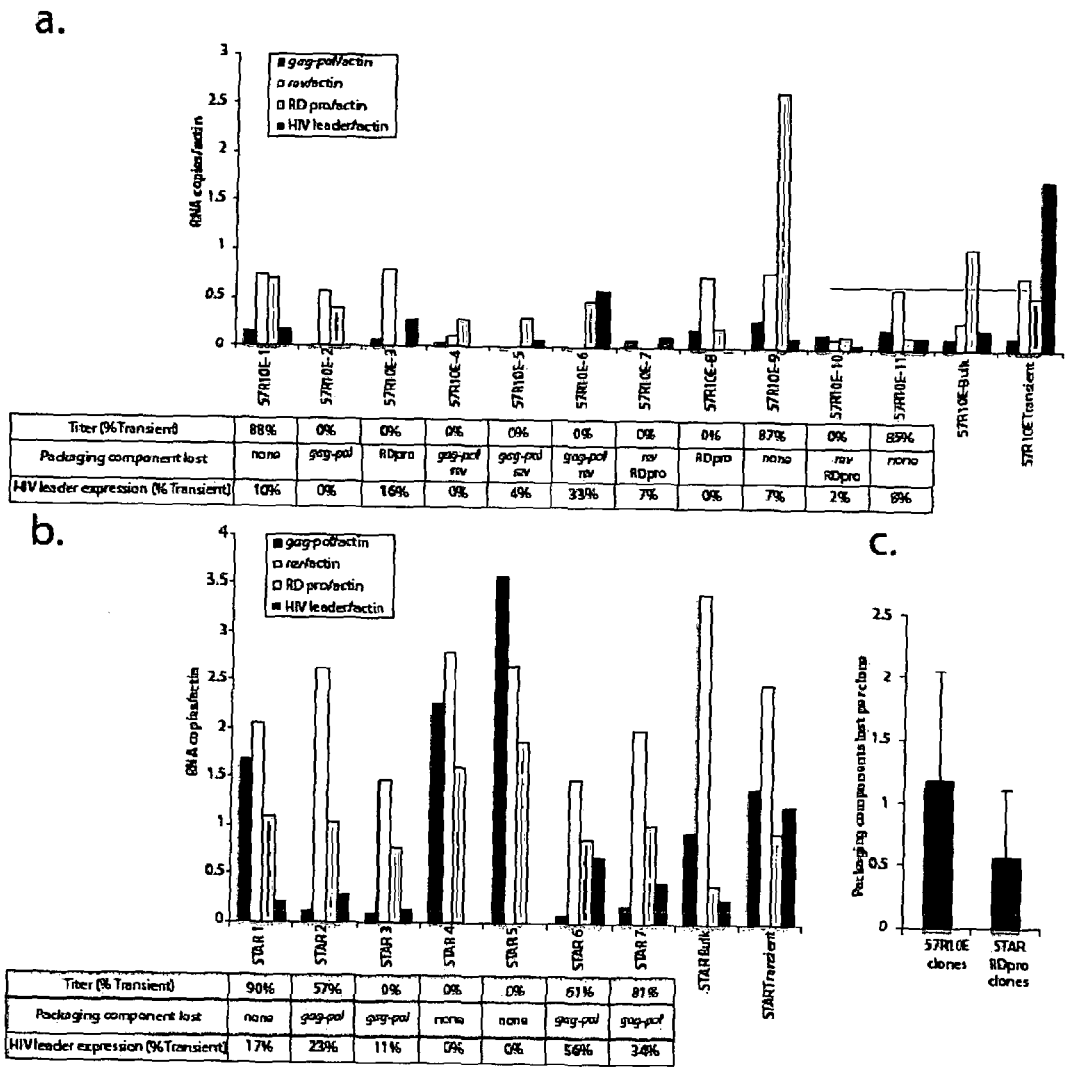
FIG. 8. Expression of the packaging components in each 57R10E and STAR RDpro clone stably transfected with SIN pHV and BSr. (a.) Q-RT-PCR for packaging components and HIV leader in 57R10E clones, the bulk population from which 57R10E clones were derived and 57R10E transiently transfected with SIN pHV. (b.) Q-RT-PCR for packaging components and HIV leader in STAR RDpro clones, the bulk population from which the STAR RDpro clones were isolated and STAR RDpro transiently transfected with SIN pHV. The table underneath each graph in (a.) and (b.), shows the titer of each clone and expression of HIV leader as percentages of transient titer after SIN pHV transfection of 57R10E or STAR RDpro. The transient titer was $3\times10^4$ iu/ml for 57R10E and $1.2\times10^5$ for STAR RDpro. In HIV leader expression, the percentages in red or green are lower or higher than bulk respectively (57R10E and STAR RDpro bulk HIV leader expression was 12% and 20% of the transient expression respectively). Packaging components expressed at less than 50% of 57R10E or STAR transiently transfected with SIN pHV are also listed as 'Packaging component lost'. (c.) The average number of packaging components below 50% per clone is shown for 57R10E and STAR RDpro clones. The difference between 57R10E and STAR RDpro clones was not significant (p=0.136, Mann Whitney test).
Figure 9:
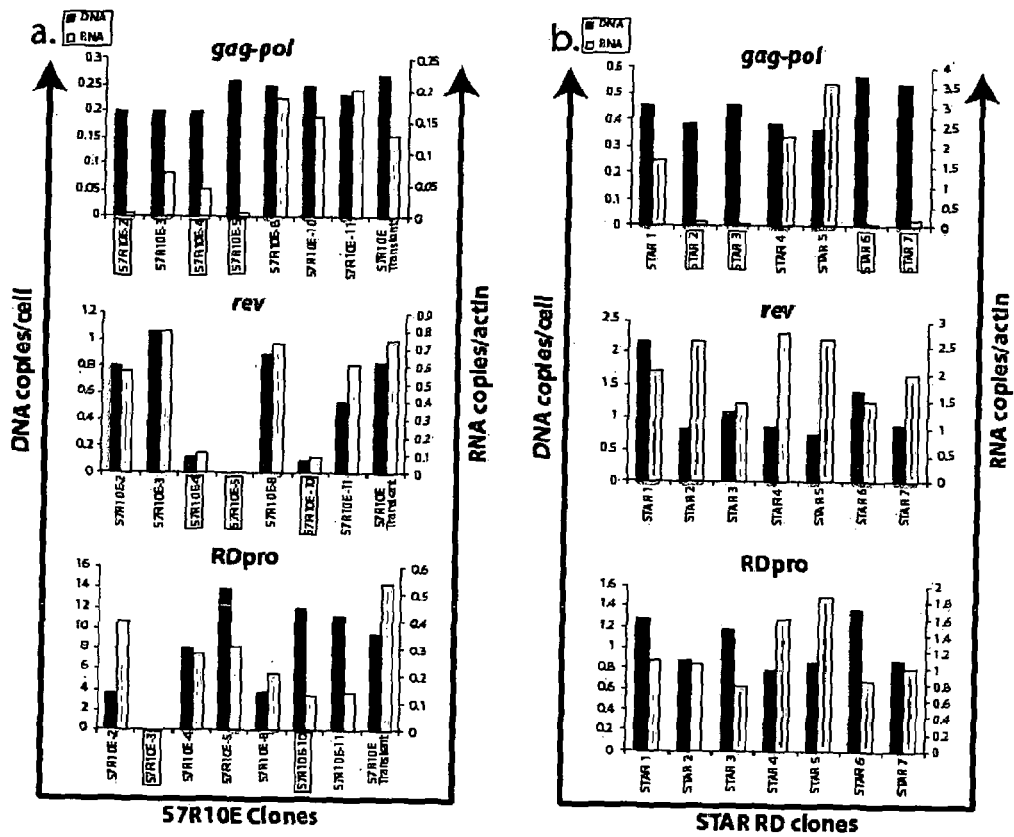
FIG. 9. (a.) RNA and DNA quantities of each packaging component in 57R10E clones, measured by QPCR. (b.) RNA and DNA quantities of each packaging component in STAR RDpro clones, measured by QPCR. In both (a.) and (b.), the red boxes enclose the clones with more than a 50% loss in RNA expression after stable transfection. The number of RNA copies in each reaction was normalised to the number of actin RNA copies in a parallel reaction. The number of DNA copies in each reaction was normalised to the number of cells giving rise to the gDNA in each reaction. The number of cells was quantified by QPCR for actin in a parallel reaction and divided by 4, assuming a tetraploid genome.

An observation throughout FIGS. 8 and 9, is that STAR RDpro clones seem to have a higher expression of packaging components compared to 57R10E clones. This is important, as if STAR RDpro cells express higher levels of packaging components than is required for vector production, losses in expression may not be functionally significant. This is illustrated by START, which made a titer of over $10^4$ infectious units/ml despite only expressing 12% of the gag-pol RNA expressed by STAR RDpro prior to stable transfection.

Figure 10:
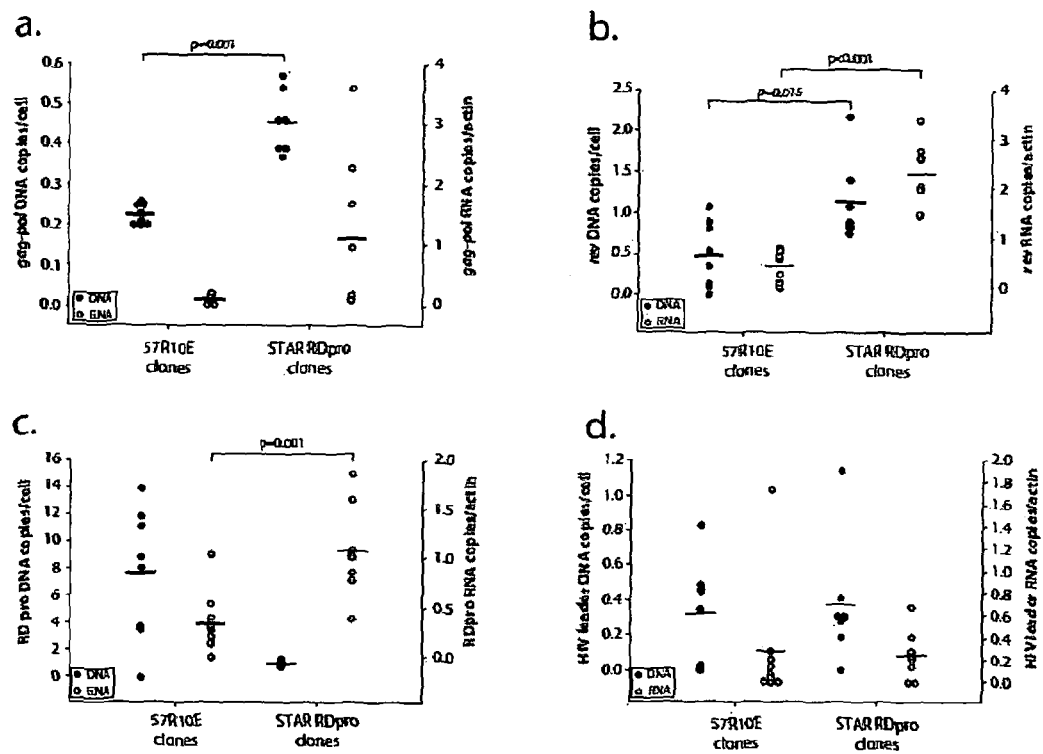
FIG. 10. Comparison of DNA and RNA quantities between 57R10E clones and STAR RDpro clones. Quantities were measured by QPCR and are presented as individual data sets in FIGS. 5.9. If the data passed the normality and equal variance tests, the t-test was used otherwise the Mann Whitney test was used. (a.) There was a significant difference in gag-pol DNA copies between 57R10E clones and STAR clones (p=0.001, t-test), but no significant difference in gag-pol RNA (p=0.06, Mann Whitney test), despite substantially higher levels of gag-pol RNA in some STAR RDpro clones, implying that more clones would be needed to accurately determine the difference. (b.) There was a significant difference in both rev DNA (p=0.016, t-test) and RNA (p<0.001, t-test) quantities between 57R10E and STAR RDpro clones. (c.) There was no significant difference in RDpro DNA quantity between 57R10E and STAR clones (p=1, t-test), but there was a significant difference in RDpro RNA quantity (p=0.001, t-test). (d.) There was no significant difference in HIV leader DNA (0.774, t-test) or RNA (P=0.499, Mann Whitney test) between 57R10E and STAR RDpro clones.

Pooling the data on packaging component RNA and DNA allowed comparison of 57R10E and STAR RDpro clones. STAR RDpro clones appeared to have higher levels of RNA for all the packaging components, although this only reached significance for rev and RDpro (FIGS. 10b and c). Some STAR RDpro clones had a substantially higher gag-pol RNA level than 57R10E clones, however other STAR RDpro clones had lost expression completely, which is probably the reason for the lack of statistical difference between 57R10E clones and STAR RDpro clones in gag-pol RNA (FIG. 10a). Thus, more clones would need to be analysed to accurately determine the significance of the difference in gag-pol RNA. The differences in DNA between 57R10E and STAR RDpro in gag-pol and rev were significant (FIGS. 10a and b), which is consistent with our assumption that STAR RDpro has more copies of gag-pol and rev due to transduction with MLV vectors at a high MOI. The lack of a significant difference in RDpro DNA copies (FIG. 10c) is also consistent with the fact that the same method of stable expression was used for both 57R10E and STAR RDpro cell lines, however as detailed above, the large number of RDpro DNA copies in some 57R10E clones is unexplained.

Finally, SIN pHV vector genome DNA or RNA quantities were not significantly different between 57R10E and STAR RDpro clones (FIG. 10d). This indicates that stable transfection of SIN pHV worked equally well in STAR RDpro and 57R10E and the differences in titer are thus more likely to be due to packaging component differences than anything to do with vector genome expression.

In contrast to STAR RDpro, antibiotic resistance genes were used to select for stable expression of all the packaging components in 57R10E. Therefore, there was the possibility that gag-pol, rev and RDpro expression could be re-selected using the antibiotics used in the original selections of each packaging component.

Re-Selection Before Stable Transfection

Figure 11:
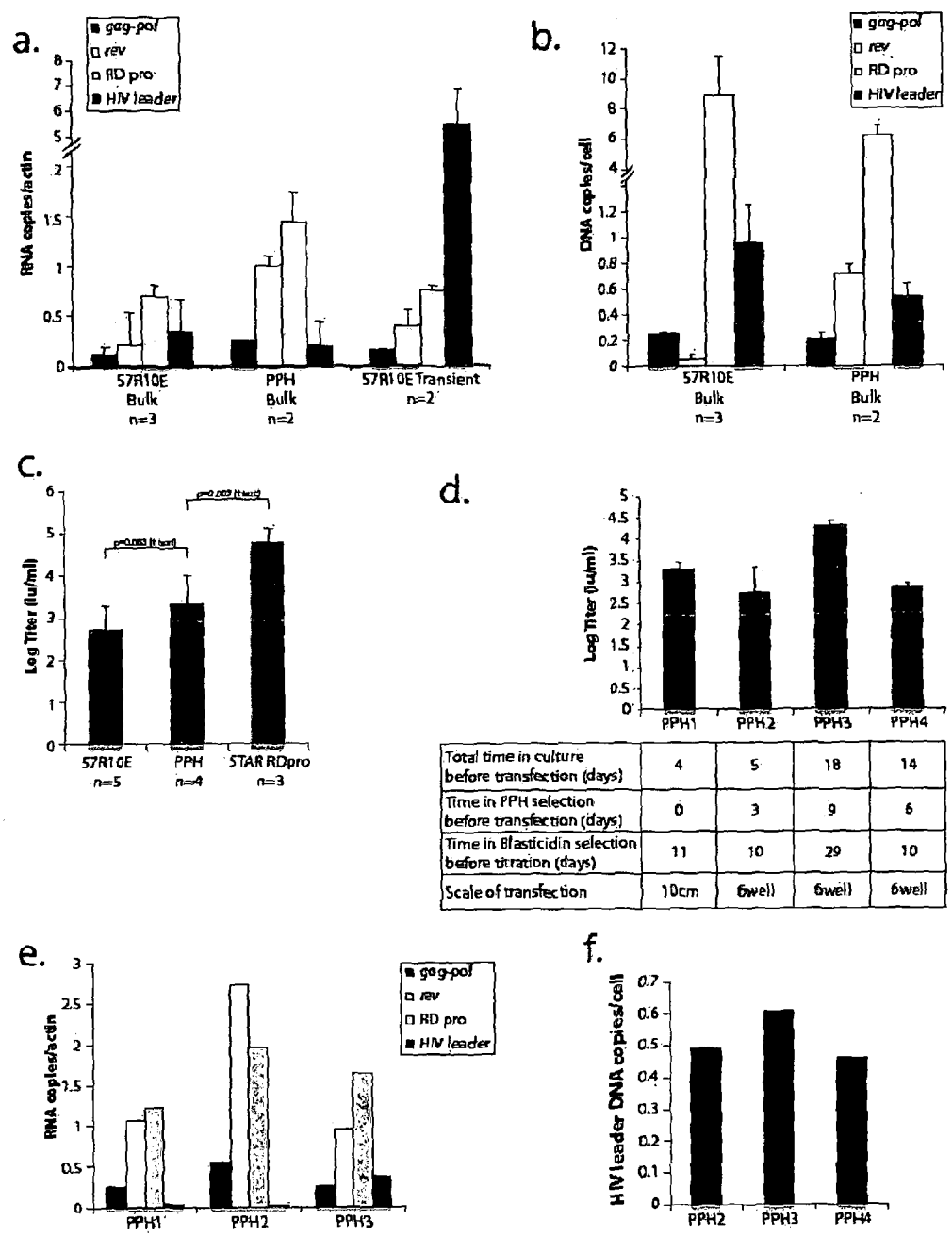
FIG. 11. Re-selection of packaging components before stable transfection of SIN pHV and BSr. Note, 'PPH' refers to 57R10E cultured with puromycin, phleomycin and hygromycin before or during transfection. (a.) Average packaging component and HIV leader RNA quantities from bulk blasticidin resistant cultures. The number of experiments is shown (NB, for PPH, q-RT-PCR data from PPH 1 and 3 was used). (b.) Average DNA quantities of packaging components and HIV leader in bulk cultures of blasticidin resistant cells. (c.) Average bulk titers after stable transfection of SIN pHV and BSr in 57R10E, PPH and STAR RDpro. The number of stable transfections is shown, and significant differences indicated, with the test used in brackets. (d.) Titers of bulk blasticidin resistant cultures of each stable transfection experiment on PPH (PPH 1-4). The table underneath details the experiment protocol in each stable transfection with SIN pHV and BSr. In each experiment stable integrants were selected using blasticidin. (e.) Expression of packaging components and HIV leader in Bulk blasticidin resistant cultures from the indicated stable transfections (PPH 1-3). (f.) H1V leader DNA copies/cell (by QPCR) in PPH2 (bulk culture selected in blasticidin and phleomycin), PPH3 and 4. Cells were selected with blasticidin and phleomycin in the PPH2 experiment, while only blasticidin was used for the others.

In an attempt to ensure that the 57R10E population transfected with SIN pHV and BSr was homogenously expressing high levels of gag-pol, rev and RDpro, in one set of experiments, 57R10E was cultured in puromycin, hygromycin and phleomycin. In all experiments where re-selection of packaging components in 57R10E was carried out either before or during transfection, the cell line has been referred to as 'PPH'. PPH bulk had higher levels of expression of gag-pol, rev and RDpro than 57R10E bulk and 57R10E transiently transfected with SIN pHV (FIG. 11a). Interestingly, rescue of rev RNA was associated with increase in rev DNA copies/cell in PPH bulk populations, possibly indicating enrichment of cells retaining high copies of rev DNA. This was in contrast to the increases in gag-pol and RDpro in PPH bulk, which largely appeared to happen at the RNA rather than the DNA level (FIG. 11b).

Despite increased packaging component expression the titer of PPH bulk was not significantly different from 57R10E bulk on average (FIG. 11c). It was noted that different PPH selection followed by blasticidin selection protocols were used and one PPH bulk culture (PPH3) made a titer of over $10^4$ infectious units per ml, while the PPH cultures in the other experiments yielded much lower titers. The packaging component expression in PPH populations appeared to be similar between different experiments, but PPH3 had a much higher expression of HIV leader RNA than the other two PPH bulk populations (FIG. 11e). No such remarkable difference was observed for HIV leader DNA copies/cell (FIG. 11f). As this bulk culture was cultured for longer in blasticidin selection than the other PPH bulk cultures, more stable expression of BSr, and therefore any linked SIN pHV, may have been selected.

In summary, PPH selection before stable transfection was able to increase packaging component expression during stable transfection. One PPH culture stably transfected with a SIN LTR HIV vector had a titer higher than $10^4$ infectious units/ml. This bulk culture did not have more vector genome DNA copies per cell than the other PPH bulk cultures, but had substantially higher levels of vector genome RNA as assessed by QPCR for HIV leader.

Figure 12:
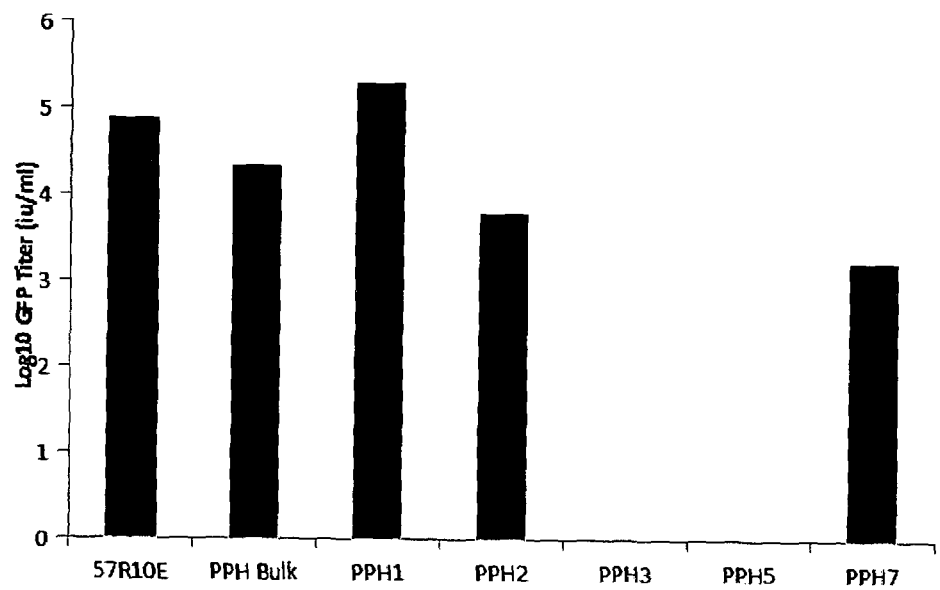
FIG. 12. Cloning of pSIN-HV producer cells following PPH3 culture. Clonal cell cultures were established by limiting dilution of the PPH3 culture in the presence of blasticidin and expanded. Supernatants were harvested after overnight culture in the medium without blasticidin and titrated for GFP transduction on 293T cells.

Cloning of pSIN-HV Vector Producer Cells Following PPH Re-Selection pSIN-HV producer cells were cloned from the PPH3 culture which had the highest titre among the PPH selected bulk producer cells under blasticidin selection. Initially 5 clones (PPH3-c1, 2, 3, 5, 7) were selected and their supernatants were titrated on 293T cells (FIG. 12). One of these clones, PPH3-c1 had more than 10E5 GFP i.u./ml, which may be clinically useful.

Long-Term Vector Production by PPH3-c1 Clone.

Figure 13:
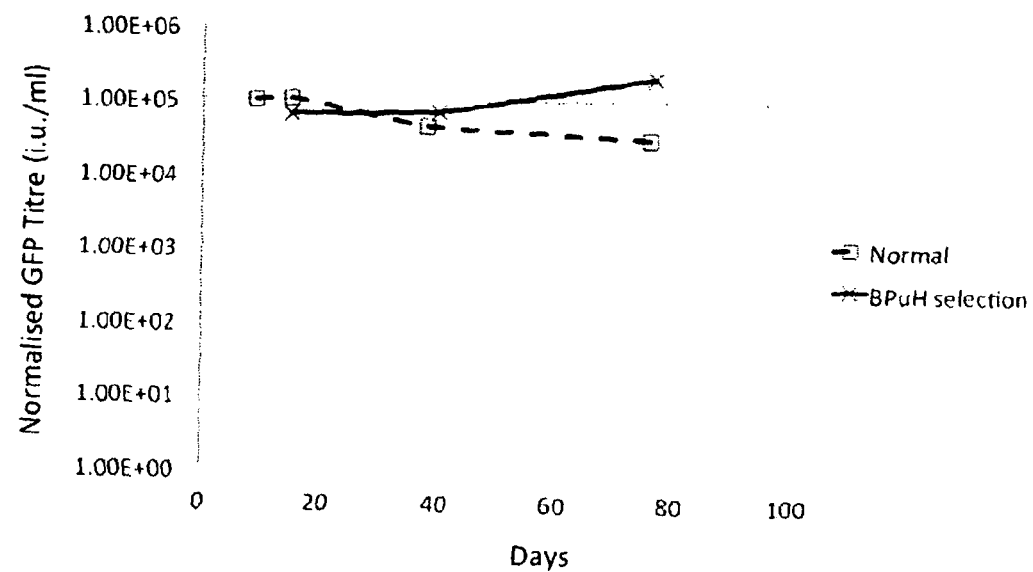
FIG. 13. Time course of vector production by the PPH3-c1 clone. A frozen stock of PPH3-c1 cells were put in culture in either the normal medium or the selection medium containing blasticidin, puromycin and hygromycin (BPuH selection) at Day 1 and cultured. Supernatants were harvested at various time points up to Day 78 after overnight culture in the normal medium and titrated for GFP transduction on 293T cells. Titers normalized to that of STAR/RD/pHV to be 10E6 are shown FIG. 14. Vector production by further PPH3 clones kept under BPuH selection. Clonal cells were cultured in BPuH medium for 10 days or longer. Supernatants were harvested after overnight culture in the normal medium and titrated for GFP transduction on 293T cells.

An early frozen stock of PPH3-c1 cells were thawed and put in culture in either normal medium or medium with blasticidin, puromycin and hygromycin (BPuH selection) at Day 1 and supernatants were harvested periodically up to about Day 80. Supernatants were titrated on 293T cells along with control supernatants from STAR/RD/pHV. Titers normalized to that of STAR/RD/pHV to be 10E6 are shown in FIG. 13A. While gradual reduction of titre was observed for PPH3-c1 in normal culture, cells cultured in BPuH selection media retained their high titre.

Repeated Cloning of High Titre Producers

Figure 14:
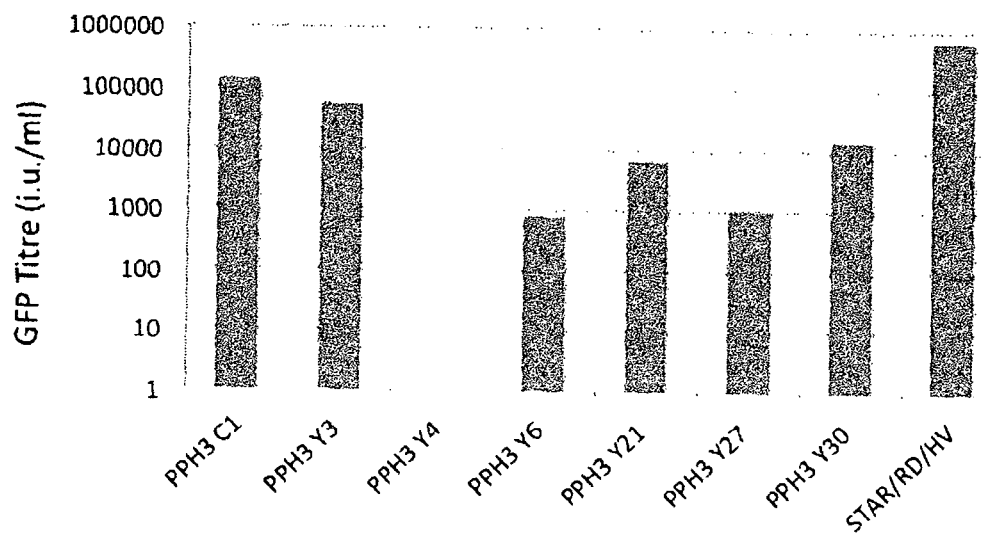

Cell cloning process was repeated in the medium containing blasticidin. Puromycin and hygromycin were further added to the medium after establishment of clones. Supernatants of these clones (PPH3-Y series) were titrated (FIG. 14). One (PPH3-Y3) of about 30 clones selected gave a titre near 10E5. In summary re-selection of 57R10E cells with PPH afforded high titre producer clones that give titres around 10E5, albeit in a limited frequency. One of these clones has achieved a long-term (almost 80 days) production of high titer vectors.

Further Verification

For the purposes of this section the 57R10 cells and 57R10E cells will be referred to as WinPac and WinPac-RDpro cells, respectively, but for the avoidance of doubt, WinPac cells are 57R10 cells.

WinPac-RDpro cells are 57R10E cells.

WinPac-RDpro-HV cells are derived from 57R10E cells after stable co-transfection of GFP-encoding vector genome and pSELECT Blasti MCS.

Figure 15:
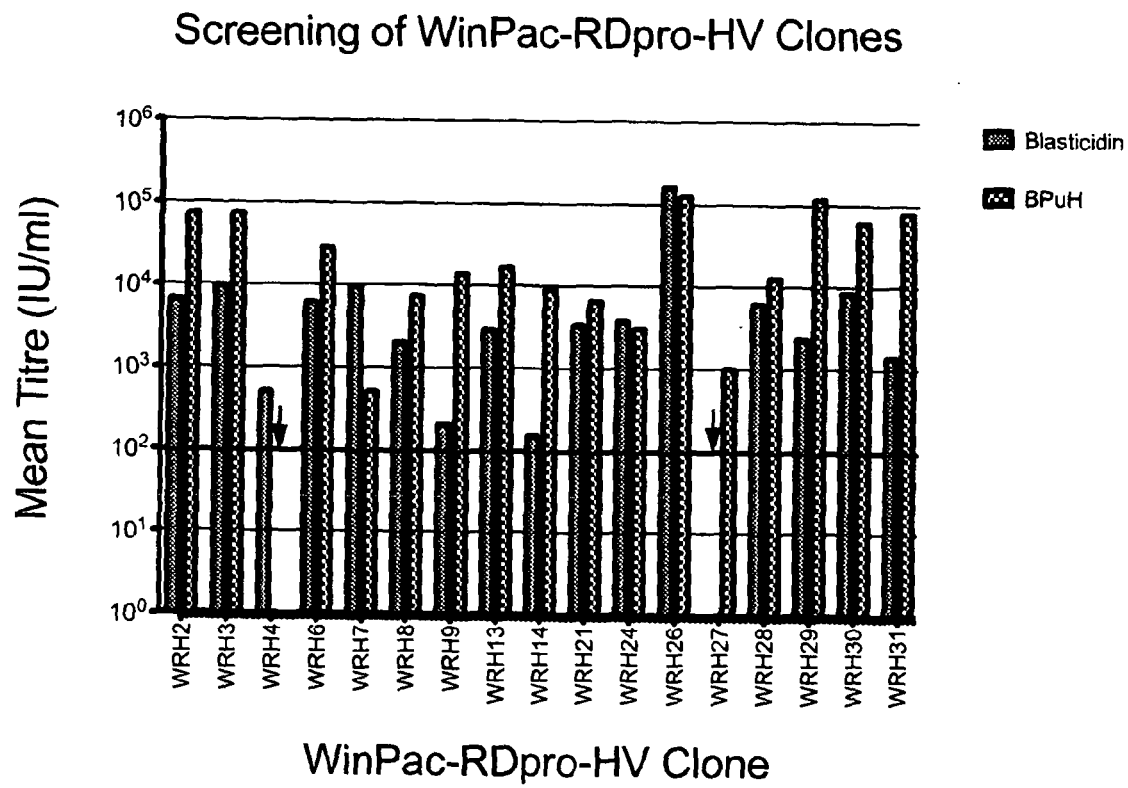
FIG. 15. Screening of WinPac-RDpro-HV clones. Single clones were isolated from a bulk population of packaging cells growing in Blasticidin (antibiotic selecting for expression of vector genome). 21 Clones were isolated and grown in the presence of Blasticidin alone then in the presence of Blasticidin+Puromycin (selects for Gag/Pol expression)+Hygromycin (selects for Rev expression). For the clones that survived antibiotic selection, vector-containing medium (VCM) was harvested, filtered and titrated on 293T cells.

A packaging cell line would be able to meet clinical trial requirements at a feasible and practical production scale if it produced a high titre of infectious units per ml, e.g. preferably at least $10^4$ infectious units per ml, or more preferably at least $10^5$ infectious units per ml. The inventors have screened a number of WinPac-RDpro HV clones (see FIG. 15) and three high-titre clones were identified. WinPac-Rdpro-HV2 (titres went above $10^5$ IU/ml after selection with phleomycin which selects for RDpro env expression), Win-Pac-RDpro-HV26 and WinPac-Rdpro-HV29 (see FIG. 15).

The inventors have also shown that titres can be optimised (see FIG. 16). This was achieved by growing cells in the presence of antibiotics which select for expression of all packaging components and vector genome (Blasticidin+Phleomycin+Puromycin+Hygromycin (BPlPuH)). When the cells reached confluence of ~90 to 100%, they were washed and medium was replaced with 15 ml of fresh complete medium. 24 hours later, vector containing medium (VCM) was collected, passed through 0.45 µm filter, and stored at −80° C. To optimise titrations, 5-fold serial dilutions of VCM were used to transduce 6×10$^5$ 293T cells per well of a 12-well plate in a total volume of 0.5 ml at transduction in the presence of 8 µg/ml polybrene. 12 hrs post-transduction, 0.5 ml of fresh complete medium was added. 24 hrs post-transduction, medium was replaced with 2.5 ml of fresh complete medium. 48 hrs post-transduction, cells were harvested, fixed and analysed for GFP expression by FACS. The use of spinoculation (centrifugal inoculation) increases the titre in all samples (see FIG. 16).

The inventors have also appreciated that for packaging cells to be practically useful, stable titres should be maintained over a long period of culture. In order to investigate this, the inventors kept clones in culture with or without BPIPuH (Blasticidin+Phleomycin+Puromycin+Hygromycin). VCM was harvested and titrated at ~3 to 4 week intervals. The inventors found that titres were relatively stable over a period of at least 5 months especially when cultured in the presence of a selection of antibiotics (see FIG. 17).

The inventors have further demonstrated the ability to rescue titres by re-selecting with antibiotics and that high titres can be maintained after removal of antibiotics (see FIG. 18).

Concentrating vectors by ultracentrifugation allows the transduction of primary human cells at clinically relevant multiplicity of infection (MOIs) using minimal volume of concentrated supernatants. To show that the vector particles of the present invention could achieve reasonable concentration, vector containing medium collected from one clone was concentrated by ultracentrifugation and resuspended in serum-free medium. Titres were determined on 293T cells before and after concentration which demonstrated the practicality of concentrating the RDpro-pseudotyped vectors produced by WinPac-RDpro-HV cells (see FIG. 19).

The inventors have further investigated whether the clones can be maintained in a serum-free or serum-reduced environment. Animal serum is commonly used as a supplement in cell culture medium and is thought to be important for producing retroviral vectors at high titre. However, they have a variable and poorly characterised composition and are a potential source of contamination, infection and/or immunogens. Accordingly, it may be preferable to harvest vectors in a serum-free environment. FIG. 20 shows the results of harvesting vectors in serum-free and serum-reduced medium. This provided one clone that is able to produces lentiviral particles at a constant level even when harvested in serum-free medium. The inventors have also shown that the vectors harvested in serum-free medium can also be concentrated by ultracentrifugation (results not shown).

The inventors have investigated whether the clones exhibit stable vector genome levels. As shown in FIG. 21, the absence of large increases in vector genome DNA copy no./cell excludes the presence of significant auto-transduction. Moreover, the stability of Gag-Pol DNA copy number in all tested clones supports the premise that Gag-Pol is not being cross-packaged into virions.

The inventors have also investigated RNA expression levels at the time of VCM harvest. FIG. 22 shows that lentiviral vector titres remain high at later time points even when vector RNA levels are reduced. The data suggests that the stoichiometry of various vector components as well as their absolute level of expression may influence titres.

The inventors also investigate whether the HIV-1 restriction factor A3G, which can be packaged in virions and subsequently mutate the proviral genome in target cells, was present in the packaging cells at detectable levels. FIG. 23 shows that A3G was not detectable in STAR, WinPac or 293T cells.

DISCUSSION

Two lentiviral vector packaging cell lines derived from 293FT cells were evaluated. The first, clone F stably expressed HIV gag-pol, rev and RD114 env. This packaging cell line produced a titer below $10^4$ infectious units per ml when transiently transfected with a lentiviral vector. Stable transfection of a SIN lentiviral vector led to the isolation of one clone that SUBSTITUTE SHEET (RULE 26) produced a titer of over $10^4$ infectious units per ml for over 70 days in culture. Furthermore, each packaging component and vector genome expression in this clone was stable over the same time period. This finding demonstrated that a stable packaging cell line could be constructed in 293FT cells using a protocol more suitable for clinical application than that used to make STAR cells. Secondly, it showed that stable transfection of a SIN lentiviral vector could lead to the isolation of a producer clone with a titer higher than transient transfection of the packaging cell line with the same vector. However, the titer obtained with the producer clone FS9 was too low to be useful in vector production for clinical trials.

Another packaging cell line was developed in parallel by the inventors. In this approach, HIV gag-pol was stably expressed by RMCE into a tagged 'high expresser site'. Stable transfection of rev and RDpro led to the isolation of clone 57R10E, which has a similar level of gag-pol, and higher levels of rev and RD114 env in comparison to clone F. A titer of over $10^4$ infectious units per ml was obtained in 57R10E after transient transfection of a SIN lentiviral vector. Given the results from the first packaging cell line, some producer clones obtained from 57R10E might be expected to produce a titer of over $10^5$ infectious units per ml, which is sufficient for production of vectors for clinical trials. To achieve this re-selection of 57R10E cells with 3 drugs, puromycin, hygromycin and phleomycin, was required before and during transfection of the vector construct. Screening of limited number of clones (ca 35 clones) gave rise to two clones that give titres around 10E5, suggesting clinical useful clones can be obtained by screening a larger number of clones after strict drug re-selection of 57R10E cells.

REFERENCES

1. Cartier, N., S. Hacein-Bey-Abina, C. C. Bartholomae, G. Veres, M. Schmidt, I. Kutschera, M. Vidaud, U. Abel, L. Dal-Cortivo, L. Caccavelli, N. Mahlaoui, V. Kiermer, D. Mittelstaedt, C. Bellesme, N. Lahlou, F. Lefrere, S. Blanche, M. Audit, E. Payen, P. Leboulch, B. l'Homme, P. Bougneres, C. Von Kalle, A. Fischer, M. Cavazzana-Calvo, and P. Aubourg. 2009. Hematopoietic stem cell gene therapy with a lentiviral vector in X-linked adrenoleukodystrophy. Science 326:818-823.
2. Cavazzana-Calvo, M., E. Payen, O. Negre, G. Wang, K. Hehir, F. Fusil, J. Down, M. Denaro, T. Brady, K. Westerman, R. Cavallesco, B. Gillet-Legrand, L. Caccavelli, R. Sgarra, L. Maouche-Chretien, F. Bernaudin, R. Girot, R. Dorazio, G. J. Mulder, A. Polack, A. Bank, J. Soulier, J. Larghero, N. Kabbara, B. Dalle, B. Gourmet, G. Socie, S. Chretien, N. Cartier, P. Aubourg, A. Fischer, K. Cornetta, F. Galacteros, Y. Beuzard, E. Gluckman, F. Bushman, S. Hacein-Bey-Abina, and P. Leboulch. 2010. Transfusion independence and HMGA2 activation after gene therapy of human beta-thalassaemia. Nature 467:318-322.
3. Cockrell, A. S., H. Ma, K. Fu, T. J. McCown, and T. Kafri. 2006. A trans-lentiviral packaging cell line for high-titer conditional self-inactivating HIV-1 vectors. Mol Ther 14:276-284.
4. Di Nunzio, F., B. Piovani, F. L. Cosset, F. Mavilio, and A. Stornaiuolo. 2007. Transduction of human hematopoietic stem cells by lentiviral vectors pseudotyped with the RD114-TR chimeric envelope glycoprotein. Hum Gene Ther 18:811-820.
5. Dull, T., R. Zufferey, M. Kelly, R. J. Mandel, M. Nguyen, D. Trono, and L. Naldini. 1998. A third-generation lentivirus vector with a conditional packaging system. J Virol 72:8463-8471.
6. Farson, D., R. Witt, R. McGuinness, T. Dull, M. Kelly, J. Song, R. Radeke, A. Bukovsky, A. Consiglio, and L. Naldini. 2001. A new-generation stable inducible packaging cell line for lentiviral vectors. Hum Gene Ther 12:981-997.
7. Ikeda, Y., Y. Takeuchi, F. Martin, F. L. Cosset, K. Mitrophanous, and M. Collins. 2003. Continuous high-titer HIV-1 vector production. *Nat Biotechnol* 21:569-572.

8. Ikeda, Y., L. M. Ylinen, M. Kahar-Bador, and G. J. Towers. 2004. Influence of gag on human immunodeficiency virus type 1 species-specific tropism. J Virol 78:11816-11822.
9. Kafri, T., H. van Praag, L. Ouyang, F. H. Gage, and I. M. Verma. 1999. A packaging cell line for lentivirus vectors. J Virol 73:576-584.
10. Klages, N., R. Zufferey, and D. Trono. 2000. A stable system for the high-titer production of multiply attenuated lentiviral vectors. Mol Ther 2:170-176.
11. Levine, B. L., L. M. Humeau, J. Boyer, R. R. MacGregor, T. Rebello, X. Lu, G. K. Binder, V. Slepushkin, P. Lemiale, J. R. Mascola, F. D. Bushman, B. Dropulic, and C. H. June. 2006. Gene transfer in humans using a conditionally replicating lentiviral vector. Proc Natl Acad Sci USA 103:17372-17377.
12. Relander, T., M. Johansson, K. Olsson, Y. Ikeda, Y. Takeuchi, M. Collins, and J. Richter. 2005. Gene transfer to repopulating human CD34+ cells using amphotropic-, GALV-, or RD114-pseudotyped HIV-1-based vectors from stable producer cells. Mol Ther 11:452-459.
13. Sandrin, V., B. Boson, P. Salmon, W. Gay, D. Negre, R. Le Grand, D. Trono, and F. L. Cosset. 2002. Lentiviral vectors pseudotyped with a modified RD114 envelope glycoprotein show increased stability in sera and augmented transduction of primary lymphocytes and CD34+ cells derived from human and nonhuman primates. Blood 100:823-832.
14. Sparacio, S., T. Pfeiffer, H. Schaal, and V. Bosch. 2001. Generation of a flexible cell line with regulatable, high-level expression of HIV Gag/Pol particles capable of packaging HIV-derived vectors. Mol Ther 3:602-612.
15. Stewart, H. J., L. Fong-Wong, I. Strickland, D. Chipchase, M. Kelleher, L. Stevenson, V. Thoree, J. McCarthy, G. S. Ralph, K. A. Mitrophanous, and P. A. Radcliffe. 2011. A stable producer cell line for the manufacture of a lentiviral vector for gene therapy of Parkinson's disease. Hum Gene Ther 22:357-369.
16. Stewart, H. J., M. A. Leroux-Carlucci, C. J. Sion, K. A. Mitrophanous, and P. A. Radcliffe. 2009. Development of inducible EIAV-based lentiviral vector packaging and producer cell lines. Gene Ther 16:805-814.
17. Strang, B. L., Y. Ikeda, F. L. Cosset, M. K. Collins, and Y. Takeuchi. 2004. Characterization of HIV-1 vectors with gammaretrovirus envelope glycoproteins produced from stable packaging cells. Gene Ther 11:591-598.
18. Throm, R. E., A. A. Ouma, S. Zhou, A. Chandrasekaran, T. Lockey, M. Greene, S. S. De Ravin, M. Moayeri, H. L. Malech, B. P. Sorrentino, and J. T. Gray. 2009. Efficient construction of producer cell lines for a SIN lentiviral vector for SCID-X1 gene therapy by concatemeric array transfection. Blood 113:5104-5110.

What is claimed is:

1. A method for producing a cell which constitutively expresses lentiviral gag and pol proteins, comprising the steps of
   (i) providing a target cell comprising a single copy per cell of an exogenous nucleic acid construct integrated into a transcriptionally active chromosomal locus in the cell genome, wherein the integrated nucleic acid construct is a retroviral provirus having a 5' long terminal repeat (LTR) comprising a U3 and R-region, a 3' LTR comprising a U3 and R-region, said construct comprising a first and a second mutant LoxP recombinase target site positioned so as to define a target construct between them; wherein the first mutant LoxP recombinase target site is between the U3 and R-region in the 5' LTR and the second recombinase target site is between the U3 and the R-region in the 3' LTR, thereby defining the target construct;
   (ii) introducing into said cell an expression cassette comprising and nucleic acid encoding a promoterless selectable marker and lentiviral gag and pol coding sequences under the control of a constitutive promoter, said expression cassette having a LoxP recombinase target site at both the 5' and 3' ends, said 5' and 3' recombinase target sites corresponding to the first and second recombinase target sites in the integrated nucleic acid sequence respectively; and
   (iii) introducing a Cre-recombinase into the target cell and propagating the cell for recombinase-mediated exchange (RMCE) between the expression cassette and the target construct at their respective recombinase target sites, wherein the expression cassette replaces the target construct contained within the integrated retroviral provirus between 5' LTR U3 and the 3' LTR R regions, and wherein the expression cassette is integrated between a double mutant LoxP site downstream of the first 5' LTR U3 region and a LoxP site upstream of the 3' LTR R-region; and
   (iv) selecting the target cell which expresses the selectable marker under the control of the 5' U3 promoter upstream of the double mutant LoxP site, said target cell also expressing gag and pol protein.

2. The method according to claim 1 wherein the first recombinase target site is mutated to ensure directionality following recombinase-mediated cassette exchange.

3. The method according to claim 1 wherein said target construct further comprises nucleic acid encoding one or more selectable markers operably linked to a promoter; wherein said one or more selectable markers is optionally an antibiotic resistance gene or GFP marker gene.

4. The method according to claim 1 wherein the integrated nucleic acid construct is introduced into the target cell by transfection or transduction.

5. The method according to claim 1 further comprising introducing into the cell a coding sequence which expresses env; and/or introducing into the cell a coding sequence which expresses rev, wherein said env coding sequence and/or said rev coding sequence is part of an expression cassette and operably linked to a promoter.

6. The method according to claim 5 further comprising introducing into said target cell a plasmid containing a replication-defective lentiviral vector comprising a 5'LTR, a 3'LTR and a packaging signal wherein said replication defective lentiviral vector optionally comprises a transgene, thereby generating a producer cell.

7. The method according to claim 1 wherein said lentiviral gag and pol coding sequences are provided as a gag-pol coding sequence.

8. The method according to claim 7 wherein said lentiviral gag-pol coding sequence is a codon optimized human immunodeficiency virus (HIV) gag-pol sequence which comprises a mutation which encodes an HIV capsid protein with a histidine to glutamine change at position 87 (H87Q).

9. The method according to claim 3, further comprising determining the presence and/or expression level of the single copy integrated nucleic acid construct in the cell by detecting the selectable marker.

10. The method according to claim 9 further comprising determining the presence of a single copy integrated nucleic acid construct in the cell, wherein said determination is performed with quantitative PCR.

11. The method according to claim 1, wherein said integrated retroviral provirus is introduced into the target cell in a retroviral vector encoding a selectable marker under the control of a promoter; wherein said target cell is selected based on the expression of the selectable marker, and wherein expression of the selectable marker is indicative of said retroviral vector being integrated into the genome of the cell.

12. The method according to claim 11 wherein the retroviral vector is a murine leukemia virus (MLV) vector; and wherein the selectable marker is an antibiotic resistance gene.

13. The method according to claim 6 further comprising propagating said cell in suitable culture medium and obtaining vector particles from said culture medium.

14. The method according to claim 13 wherein said transgene is a heterologous gene encoding a marker or therapeutic protein.

* * * * *